US006551587B2

(12) United States Patent
Hallenbeck et al.

(10) Patent No.: US 6,551,587 B2
(45) Date of Patent: *Apr. 22, 2003

(54) VECTORS FOR TISSUE-SPECIFIC REPLICATION

(75) Inventors: Paul L. Hallenbeck, Gaithersburg, MD (US); Yung-Nien Chang, Cockeysville, MD (US); Yawen L. Chiang, Potomac, MD (US)

(73) Assignee: Genetic Therapy, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/210,936

(22) Filed: Dec. 15, 1998

(65) Prior Publication Data

US 2003/0012767 A1 Jan. 16, 2003

Related U.S. Application Data

(63) Continuation of application No. 08/849,117, filed as application No. PCT/US95/15455 on Nov. 28, 1995, now Pat. No. 5,998,205, which is a continuation-in-part of application No. 08/487,992, filed on Jun. 7, 1995, now abandoned, which is a continuation-in-part of application No. 08/348,258, filed on Nov. 28, 1994, now abandoned.

(51) Int. Cl.$^7$ .............................................. H61K 48/00
(52) U.S. Cl. .................. 424/93.2; 435/320.1; 435/69.1; 435/91.4; 435/455; 536/24.1; 514/44
(58) Field of Search .................. 514/44; 424/93.2, 424/69.1; 435/320.1, 91.4, 455; 536/24.1

(56) References Cited

U.S. PATENT DOCUMENTS

| 5,112,767 A | | 5/1992 | Roy-Burman et al. ... 435/320.1 |
|---|---|---|---|
| 5,324,664 A | | 6/1994 | Nunberg et al. |
| 5,358,866 A | | 10/1994 | Mullen et al. |
| 5,416,017 A | | 5/1995 | Burton et al. |
| 5,436,146 A | | 7/1995 | Shenk et al. |
| 5,529,774 A | | 6/1996 | Barba et al. |
| 5,585,096 A | | 12/1996 | Martuza et al. |
| 5,585,254 A | * | 12/1996 | Maxwell et al. .......... 435/172.3 |
| 5,591,439 A | | 1/1997 | Plotkin et al. |
| 5,601,818 A | | 2/1997 | Freeman et al. |
| 5,624,820 A | * | 4/1997 | Cooper ...................... 435/69.1 |
| 5,624,830 A | | 4/1997 | Mullen et al. |
| 5,631,236 A | | 5/1997 | Woo et al. |
| 5,677,178 A | | 10/1997 | McCormick |
| 5,691,177 A | | 11/1997 | Guber et al. |
| 5,698,443 A | | 12/1997 | Henderson et al. |
| 5,728,379 A | | 3/1998 | Martuza et al. |
| 5,747,469 A | | 5/1998 | Roth et al. |
| 5,801,029 A | | 9/1998 | McCormick |
| 5,804,407 A | | 9/1998 | Tamaoki et al. |
| 5,830,686 A | | 11/1998 | Henderson |
| 5,846,945 A | | 12/1998 | McCormick |
| 5,856,181 A | | 1/1999 | McCormick |
| 5,871,726 A | | 2/1999 | Henderson et al. |
| 5,919,652 A | * | 7/1999 | Pang et al. ................ 435/69.1 |
| 5,965,124 A | * | 10/1999 | Feinberg .................. 424/93.21 |
| 5,998,205 A | | 12/1999 | Hallenbeck et al. |
| 6,051,417 A | | 4/2000 | Henderson et al. |
| 6,057,299 A | | 5/2000 | Henderson |
| 6,080,578 A | | 6/2000 | Bischoff et al. |
| 6,133,243 A | | 10/2000 | Kirn |
| 6,136,792 A | | 10/2000 | Henderson |
| 6,197,293 B1 | | 3/2001 | Henderson et al. |
| 6,254,862 B1 | | 7/2001 | Little et al. ................. 424/93.2 |
| 6,296,845 B1 | | 10/2001 | Sampson-Johannes et al. |
| 6,432,700 B1 | | 8/2002 | Henderson et al. ...... 435/320.1 |
| 2001/0053768 A1 | * | 12/2001 | Gregory et al. |
| 2002/0068049 A1 | | 6/2002 | Henderson et al. ...... 424/93.21 |

FOREIGN PATENT DOCUMENTS

| EP | 0 415 731 A3 | 3/1991 |
|---|---|---|
| EP | 0 476 953 | 3/1992 |
| EP | 0 514 603 | 11/1992 |
| WO | WO 90/05180 | 5/1990 |
| WO | WO 92/03563 A1 | 3/1992 |
| WO | WO 93/09239 | 5/1993 |
| WO | WO 93/10218 | 5/1993 |
| WO | WO 94/13824 | 6/1994 |
| WO | WO 94/18992 | 9/1994 |
| WO | WO 95/05835 | 3/1995 |
| WO | WO 95/11984 | 5/1995 |

(List continued on next page.)

OTHER PUBLICATIONS

Miller et al., vol. 8, 803–815, 1997.*

Berkner, K.L, "Development of Adenovirus Vectors for the Expression of Heterologous Genes," *BioTechniques* 6:616–629, Eaton Publishing Company (1988).

(List continued on next page.)

*Primary Examiner*—Dave T. Nguyen
(74) *Attorney, Agent, or Firm*—Douglas A. Golightly; Thomas Savitsky; J. Timothy Meigs

(57) ABSTRACT

The invention generally relates to targeted gene therapy using recombinant vectors and particularly adenovirus vectors. The invention specifically relates to replication-conditional vectors and methods for using them. Such vectors are able to selectively replicate in a target tissue to provide a therapeutic benefit from the presence of the vector per se or from heterologous gene products expressed from the vector and distributed throughout the tissue. In such vectors, a gene essential for replication is placed under the control of a heterologous tissue-specific transcriptional regulatory sequence. Thus, replication is conditioned on the presence of a factor(s) that induces transcription or the absence of a factor(s) that inhibits transcription of the gene by means of the transcriptional regulatory sequence with this vector, therefore, a target tissue can be selectively treated.

87 Claims, 5 Drawing Sheets

FOREIGN PATENT DOCUMENTS

| | | |
|---|---|---|
| WO | WO 95/12660 | 5/1995 |
| WO | WO 95/14102 | 5/1995 |
| WO | WO 95/25807 | 9/1995 |
| WO | WO 96/01642 | 1/1996 |
| WO | WO 96/14875 | 5/1996 |
| WO | WO 96/17053 | 6/1996 |
| WO | WO 96/18418 | 6/1996 |
| WO | WO 96/33282 | 10/1996 |
| WO | WO 96/34969 | 11/1996 |
| WO | WO 96/36365 | 11/1996 |
| WO | WO 97/01358 | 1/1997 |
| WO | WO 97/29201 | 8/1997 |
| WO | WO 98/35028 | 8/1998 |
| WO | WO 98/39465 | 9/1998 |
| WO | WO 98/39466 | 9/1998 |
| WO | WO 98/39467 | 9/1998 |

OTHER PUBLICATIONS

Friedman, J.M., and Babiss, L.E., "Adenoviral Vectors and Liver Specific Gene Control," in: *Transcriptional Control Mechanisms*, New York, Alan R. Liss, Inc., pp. 421–435 (1987).

Hallenbeck, P.L., et al., "A Novel Tumor–Specific Replication–Restricted Adenoviral Vector for Gene Therapy of Hepatocellulcar Carcinoma," *Hum. Gene Ther.* 10:1721–1733, Mary Ann Liebert, Inc. (Jul. 1999).

Taneja, S.S., et al., "In vitro target specific gene therapy for prostate cancer utilizing a prostate specific antigen promoter–driven adenoviral vector," *Proc. Amer. Assn. Cancer Res.* 35:375, Abstract No. 2236, American Assn. for Cancer Research (Mar. 1994).

Abe, M. and Kufe, D., "Characterization of cis–acting elements regulating transcription of the human DF3 breast carcinoma–associated antigen (MUC1), gene," *Proc. Natl. Acad. Sci. USA* 90:282–28 (Jan. 1993).

Babiss, L.E. et al., "Cellular Promoters Incorporated into the Adenovirus Genome: Effect of Viral DNA Replication on Endogenous and Exogenous Gene Transciption," *J. Mol. Biol.* 193:643–(1987).

Blaese, R.M. et al., "In situ Delivery of Suicide Genes for Cancer Treatment," *Eur. J. Cancer 30A*(8):1190–1193 (Aug. 1994).

Brown, D., "Gene Therapy Óversold' by Researchers, Journalists," *The Washington Post*, p. A22 Dec. 8, 1995.

Chellappan, S. et al., "Adenovirus E14, simian virus 40 tumor antigen, and human papillomavi E7 protein share the capacity to disrupt the interaction between transcription factor E2F and retinoblastoma gene product," *Proc. Natl. Acad. Sci. USA* 89:4549–4553 (1992).

Chen, S.–H. et al., "Gene therapy for brain tumors: Regression of experimental gliomas by adenovirus–mediated gene transfer in vivo," *Proc. Natl. Acad. Sci. USA* 91:3054–3057 (Apr.).

Boviatsis, et al., "Antitumor Activity and Reporter Gene Transfer into Rat Brain Neoplasms Inoculated With Herpes Simplex Virus Vectors Defective in Thymidine Kinase or Ribonucleotide Reductase," *Gene Therapy*, 1:323–331 (Sep. 1994).

Chambers, et al., "Comparison of Genetically Engineered Herpes Simplex Viruses for the Treatment of Brain Tumors in a Scid Mouse Model of Human Malignant Glioma," *Proc. Natl. Acad. Sci. USA*, 92:1411–1415 (Feb. 1995).

de Foresta, et al., "La Transformation Par Le Virus SV40 Sensibilise Les Fibroblastes de Peu Human á L'L'action Lytique du Parvovirus H–I," *C.R. Soc. Biol.*, 179:276–282 (1985)).

Eiselein, et al., "Treatment of Transplanted Murine Tumors with an Oncolytic Virus and Cyclophosphamide," *Can. Res.*, 38:3817–3822 (1978).

Fresen, et al., "Elektrokinetisches Verhalten von Ehrlich–Aszites–Tumorzellen nach Infektion mit Onkolytischem Influenzavirus," *Path. Microbiol.* (Basel), 40:227–228 (1974).

Fresen, et al., "Physiocochemical Membrane Changes in Ehrlich Ascites Tumor Cells Infected with Oncolytic Influenza Virus," *Arch. Gesamte Virusforsch.*, 41:267–276 (1973).

Fresen, K.O., "Physikochemische Veränderungen der Zelloberfläche von Ehrlich Aszites–Tumorenzellen nach Infektion mit Onkolytischem Influenza–Virus," *Zentralbl. Bakt. Hyg., I.Abt. Orig. A*, 227:409–413 (1974).

Freytag, et al., "A Novel Three–Pronged Approach to Kill Cancer Cells Selectively: Comcomitant Viral, Double Suicide Gene, and Radiotherapy," *Human Gene Therapy*, 9:1323–1333 (Jun. 1998).

Furukawa, et al., "Effect of Virus–modified Tumor Cell Extracts. Autologous Mononuclear Cell Infusions and Interleukin–2 on Oncolytic Activity of Effector Cells of Patients with Advanced Ovarian Cancer," *Cancer Immunol. Immunother.*, 30:126–132 (1989).

Haj–Ahmad, et al., "Development of a Helper–Independent Human Adenovirus Vector and Its Use in the Transfer of the Herpes Simplex Virus Thymidine Kinase Gene," *J. Virol.*, 57:267–274 (1986).

Hallenbeck, et al., "Novel Tumor Specific Replication Competent Adenoviral Vectors for Gene Therapy of Cancer," from the Fifth International Conference on Gene Therapy of Cancer, San Diego, CA, Nov. 14–16, 1996, *Cancer Gene Ther.*, 3:s19 (Nov. 1996).

Hallenbeck, et al., "Novel Tumor Specific Replication Restricted Adenoviral Vector for Gene Therapy of Liver Cancer," from the Sixth International Conference on Gene Therapy of Cancer, San Diego, CA, Nov. 20–22, 1997, *Cancer Gene Ther.*, 4:s22 (Nov. 1997).

Hodes, et al., Tissue Culture and Animal Studies with an Oncolytic Bovine Enterovirus (Bovine Enterovirus 1), *Cancer Res.*, 33:2408–2414 (1973).

Jacotot, H., "Pouvoir Oncolytique in vivo du Virus de Newcastle a L'egard du Sarcome Ascitique de Yoshida," *C.R. Hebd. Seances Acad. Sci. Paris, Ser. D*, 264:2602–2603 (1967).

Kenny, et al., "Viruses as Oncolytic Agents: A New Age for 'Therapeutic' Viruses", *J. Natl. Cancer Inst.*, 86:1185–1186 (Aug. 1994).

Ko, et al., "Osteocalcin Promoter–based Toxic Gene Therapy for the Treatment of Osteosarcoma in Experimental Models," *Cancer Res.*, 56:4614–4619 (Oct. 1996).

Lorence, et al., "Newcastle Disease Virus as an Antineoplastic Agent: Induction of Tumor Necrosis Factor–α and Augmentation of Its Cytotoxicity," *J. Natl. Cancer Inst.*, 80:1305–1312 (1988).

Mettler, et al., "Virus Inoculation in Mice Bearing Ehrlich Ascitic Tumors: Antigen Production and Tumor Regression," *Infect. Immun.* 37:23–27 (1982).

Neagoe, et al., "Methods of Active Immunotherapy and Viral Oncolysis in some Forms of Cancer," *Rev. Roum. Méd.—Med. Int.*, 24:125–142 (1986).

Rodriguez, et al., "Prostate Attenuated Replication Competent Adenovirus (ARCA) CN706: A Selective Cytotoxic for Prostate-specific Antigen-positive Prostate Cancer Cells," *Cancer Res.*, 57:2559–2563 (Jul. 1997).

Schlechte, et al., "Wirtsbereichstestung von tumorselektiven Clostridiumbutyricum–Stämmen mit dem Phagen 5," *Arch. Geshwulstforsch.*, 50:53–57 (1980).

Shoham, et al., "Augmentation of Tumor Cell Immunogenicity by Viruses—An Approach to Specific Immunotherapy of Cancer," *Nat. Immun. Cell Growth Regul.*, 9:165–172 (1990).

Sinkovics, J.G., "Oncogenes–Antioncogenes and Virus Therapy of Cancer," *Anticancer Res.*, 9:1281–1290 (1989).

Sinkovics, J.G., "Programmed Cell Death (Apoptosis): Its Virological and Immunological Connections (A Review)," *Acta Microbiol. Hung.*, 38:321–334 (1991).

Sinkovics, J.G., "Viral Oncolysates as Human Tumor Vaccines," *Intern. Rev. Immunol.*, 7:259–287 (1991).

Tsypkin, et al., "The Morphology of Tumors of the Human Gastrointestinal Tract in Short–Term Organ Culture and the Reaction of these Tumors to Infection with Poliovirus," *Cancer*, 38:1796–1806 (1976).

Yamada, et al., "Overproduction of the Protein Product of a Nonselected Foreign Gene Carried by an Adenovirus Vector," *Proc. Natl. Acad. Sci. USA*, 82:3567–3571 (1985).

Yohn, et al., "Oncolytic Potentials of Nonhuman Viruses for Human Cancer. II. Effects of Five Viruses on Heterotransplantable Human Tumors," *J. Natl. Canc. Inst.*, 41:523–529 (1968).

Zieliński, et al., "Late Results of Clinical Observation on the Oncolytic Action of Adenoviruses in Cervix Uteri Carcinoma," *Nowotwory* (Poland), 19(3):217–221 (1969).

Coghlan, A., "Gene dream fades away," *New Scientist* 145:14–15 (Nov. 1995).

Cornelis, J.J. et al., "Transformation of Human Fibroblasts by Ionizing Radiation, a Chemical Carcinogen, or Simian Virus 40 Correlates with an Increase in Susceptibility to the Autonomous Parvoviruses H–1 Virus and Minute Virus of Mice," *J. Virol.* 62(5):1679–1686 (1988).

Crystal, R.G., "Transfer of Genes to Humans: Early Lessons and Obstacles to Success," *Science* 270:404–410 (Oct. 1995).

Culver, K.W. et al., "In Vivo Gene Transfer with Retroviral Vector–Producer Cells for Treatment of Experimental Brain Tumors," *Science* 256:1550–1552 (1992).

Dillon, N., "Regulating gene expression in gene therapy," *TIBTECH* 11:167–173 (May 1993).

Dooley, T.P. et al., "Transactivation of the adenovirus Ella promoter in the absence of adenovirus E1A protein is restricted to mouse oocytes and preimplantation embryos," *Development* 107:945–956 (1989).

Dynan, W.S., "Modularity in Promoters and Enhancers," *Cell* 58:1–4 (1989).

Fattaey, A. et al., "Replication of Adenovirus Mutants in Human Cancer Cells," Abstract of papers presented at the 1994 meeting on Molecular Biology of Papovaviruses and Adenoviruses, Aug. 17–Aug. 21, 1994, Cold Spring Laboratory, Cold Spring Harbor, New York.

Friedman, J.M. et al., "Cellular Promoters Incorporated into the Adenovirus Genome: Cell Specificity of Albumin and Immunoglobulin Expression," *Molec. Cell. Biol.* 6(11):3791–3797 (1986).

Fujiwara, T. et al., "A Retroviral Wild–Type p53 Expression Vector Penetrates Human Lung Caner Spheroids and Inhibits Growth by Inducing Apoptosis," *Canc. Res.* 53:4129–4133 (Sep. 1993).

Gerard, R.D. and Meidell, R.S., "Adenovirus–Mediated Gene Transfer," *TCM* 3(5):171–177 (May 1993).

Gordon, E.M. and Anderson, W.F., "Gene therapy using retroviral vectors," *Curr. Op. Biotechnol.* 5:611–616 (Dec. 1994).

Graham, F.L., "Growth of 293 Cells in Suspension Culture," *J. Gen. Virol.* 68:937–940 (1987).

Grooteclaes, M., et al., "The 6–Kilobase c–erbB2 Promoter Contains Positive and Negative Regulatory Elements Functional in Human Mammary Cell Lines," *Cancer Res.* 54:4193–4199 (Aug. 1994).

Günzburg, W.H. and Salmons, B., "Mouse Mammary Tumor Virus Mediated Transfer and Expression of Neomycin Resistance to Infected Cultured Cells," *Virology* 155:236–248 (1986).

Günzberg, W.H. and Salmons, B., "Virus vector design in gene therapy," *Molec. Med. Today* 1(9):410–417 (Dec. 1995).

Harris, J.D. et al., "Gene therapy for cancer using tumour–specific prodrug activation," *Gene Therapy* 1:170–175 (May 1994).

Hitt, M.M. and Graham, F.L., "Adenovirus E1A under the Control of Heterologous Promoters: Wide Variation in E1A Expression Levels Has Little Effect on Virus Replication," *Virology* 179:667–678 (1990).

Horvath, J. et al., "Complementation of Adenovirus Early Region 1a and 2a Mutants by Epstein–Barr Virus Immortalized Lymphoblastoid Cell Lines," *Virology* 184:141–148 (1991).

Horwitz, M.S., "Adenoviral Diseases," in *Virology*, Fields, B.N. et al., eds., Raven Press, New York, pp. 477–495 (1985).

Huber, B.E. et al., "Retroviral–mediated gene therapy for the treatment of hepatocellular carcinoma: An innovative approach for cancer therapy," *Proc. Natl. Acad. Sci. USA* 88:8039–8043 (1991).

Imperiale, M.J. et al., "Common control of the Heat Shock Gene and Early Adenovirus Genes: Evidence for a Cellular E1A–like Activity," *Molec. Cell. Biol.* 4(5):867–874 (1984).

Kaneko, S. et al., "Adenovirus–mediated Gene Therapy of Hepatocellular Carcinoma Using Cancer–specific Gene Expression," *Canc. Res.* 55:5283–5287 (Nov. 1995).

Kovarik, A., et al., "Analysis of the Tissue–specific Promoter of the MUC1 Gene," *J. Biol. Chem.* 268:9917–9926 (May 1993).

La Thangue, N.B. and Rigby P.W.J., "An Adenovirus E1A–Like Transcription Factor Is Regulated during the Differentiation of Murine Embryonal Carcinoma Stem Cells," *Cell* 49:507–513 (1987).

Ledley, F., "Nonviral Gene Therapy: The Promise of Genes as Pharmaceutical Products," *Hum. Gene Ther.* 6:1129–1144 (Sep. 1995).

Lewin, B., "Oncogenic Conversion by Regulatory Changes in Transcription Factors," *Cell* 64:303–312 (1991).

Manome, Y. et al., "Enhancer Sequences of the DF3 Gene Regulate Expression of the Herpes Simplex Virus Thymidine Kinase Gene and Confer Sensitivity of Human Breast Cancer Cells to Ganciclovir," *Canc. Res.* 54:5408–5413 (Oct. 1994).

Mastrangelo, M.J. et al., "Gene Therapy for Human Cancer: An Essay for Clinicians," *Seminars in Oncology* 23(1):4–21 (Feb. 1996).

Max–Audit, I. et al., "Transcriptional Regulation of the Pyruvate Kinase Erythroid–specific Promoter," *J. Biol. Chem.* 268:5431–5437 (Mar. 1993).

Missero, C. et al., "Skin–specific Expression of a Truncated E1a Oncoprotein Binding to p105–Rb Leads to Abnormal Hair Follicle Maturation Without Increased Epidermal Proliferation," *J. Cell Biol.* 121:1109–1120 (Jun. 1993).

Moran, E., "Interaction of adenoviral proteins with pRB and p53," *FASEB J.* 7:880–885 (Jul. 1993).

Morishita, K. et al., "A Novel Promoter for Vascular Endothelial Growth Factor Receptor (flt–1) That Confers Endothelial–specific Gene Expression," *J. Biol. Chem.* 270:27948–27953 (Nov. 1995).

Mulligan, R.C., "The Basic Science of Gene Therapy," *Science* 260:926–931 (May 1993).

Nakabayashi, H. et al., "A Position–Dependent Silencer Plays a Major Role in Repressing α–Fetoprotein Expression in Human Hepatoma," *Mol. Cell. Biol.* 11:5885–5893 (Dec. 1991).

Nakamura, Y. et al., "Adoptive Immunotherapy with Murine Tumor–specific T Lymphocytes Engineered to Secrete Interleukin 2," *Canc. Res.* 54:5757–5760 (Nov. 1994).

Ohno, T. et al., "Gene Therapy for Vascular Smooth Muscle Cell Proliferation After Arterial Injury," *Science* 265:781–784 (Aug. 1994).

Ookawa, K. et al., "Reconstitution of the RB gene suppresses the growth of small–cell lung carcinoma cells carrying multiple genetic alterations," *Oncogene* 8(8):2175–2181 (Aug. 1993).

Orkin, S.H. and Motulsky, A.G., "Report and Recommendations of the Panel to Assess the NIH Investment in Research on Gene Therapy," Published by NIH at Bethesda, MD, Dec. 7, 1995.

Osaki, T. et al., "Gene Therapy for Carcinoembryonic Antigen–producing Human Lung Cancer Cells by Cell Type–specific Expression of Herpes Simplex Virus Thymidine Kinase Gene," *Canc. Res.* 54:5258–5261 (Oct. 1994).

Pang, S. et al., "Prostate Tissue Specificity of the Prostate–Specific Antigen Promoter Isolated from a Patient with Prostate Cancer," *Human Gene Therapy* 6:1417–1426 (Nov. 1995).

Pennisi, E., "Will a Twist of Viral Fate Lead To a New Cancer Treatment?" *Science* 274:342–343 (Oct. 1996).

Pulsieux, A. et al., "p53 as a growth suppressor gene in HBV–related hepatocellular carcinoma cells," *Oncogene* 8:487–490 (Feb. 1993).

Richards, C.A. et al., "Transcriptional Regulatory Suquences of Carcinoembryonic Antigen: Identification and Use with Cytosine Deaminase for Tumor–Specific Gene Therapy," *Human Gene Therapy* 6:881–893 (Jul. 1995).

Ringold, G.M. et al., "Glucocorticoid–stimulated accumulation of mouse mammary tumor virus RNA: Increased rate of synthesis of viral RNA," *Proc. Natl. Acad. Sci. USA* 74(7):2879–2883 (1977).

Russell, S.J. et al., "Transformation–Dependent Expression of Interleukin Genes Delivered by a Recombinant Parvovirus," *J. Virol.* 66(5):2821–2828 (1992).

Russell, S.J., "Replicating vectors for gene therapy of cancer: risks, Limitations and prospects," *Eur. J. Cancer* 30A(8):1165–1171 (Aug. 1994).

Salmons, B. and Günzburg, W.H., "Targeting of Retroviral Vectors for Gene Therapy," *Human Gene Therapy* 4:129–141 (Apr. 1993).

Schrewe, H. et al., "Cloning of the Complete Gene for the Carcinoembryonic Antigen: Analysis of Its Promoter Indicates a Region Conveying Cell Type–Specific Expression," *Molec. Cell. Biol.* 10(6):2738–2748 (1990).

Shenk, T. et al., "Functional Analysis of Adenovirus–5 Host–range Deletion Mutants Defective for Transformation of Rat Embryo Cells," *Cold Spring Harbor Symp. Quant. Biol.* 44:367–375 (1979).

Shimizu, E. et al., "RB protein status and clinical correlation from 171 cell lines representing lung cancer, extrapulmonary small cell carcinoma, and mesothelioma," *Oncogene* 9:2441–2448 (Sep. 1994).

Shingu, M. et al., "Therapeutic effects of bovine enterovirus infection on rabbits with experimentally induced adult T cell leukemia," *J. Gen. Virol.* 72:2031–2034 (1991).

Sikora, K., "Genetic approaches to cancer therapy," *Gene Therapy* 1:149–151 (Jan. 1994).

Smith, M.J. et al., "Surfactant protein A–directed toxin gene kills lung cancer cells in vitro," *Hum. Gene Ther.* 5(1):29–35 (Jan. 1994).

Spergel, J.M. and Chen–Kiang, S., "Interleukin 6 enhances a cellular activity that functionally substitutes for E1A protein in transactivation," *Proc. Natl. Acad. Sci. USA* 88:6472–6476 (1991).

Spergel, J.M. et al., "NF–IL6, a Member of the C/EBP Family, Regulates E1A–Responsive Promoters in the Absence of E1A," *J. Virol.* 66(2):1021–1030 (1992).

Stratford–Perricaudet, L. and Perricaudet, M., "Gene transfer into animals: the promise of adenovirus," *Human Gene Transfer* 219:51–61 (1991).

Vile, R.G. and Hart, I.R., "Use of Tissue–specific Expression of the Herpes Simplex Virus Thymidine Kinase Gene to Inhibit Growth of Established Murine Melanomas following Direct Intratumoral Injection of DNA," *Canc. Res.* 53:3860–3864 (Sep. 1993).

Vile, R.G. and Hart, I.R., "In Vitro and in Vivo Targeting of Gene Expression to Melanoma Cells," *Canc. Res.* 53:962–967 (Mar. 1993).

Vile, R., "Gene Therapy and Cytokines," *British Journal of Cancer* 69(Supp. 21):3 Abstract S7 (Mar. 1994).

Vile, R., "Direct Gene Transfer to Tumour Cells In Vivo," *Gene Therapy* 1(Supp. 2):S6 Abstract A23 (Nov. 1994).

Vile, R.G. et al., "Strategies for achieving multiple layers of selectivity in gene therapy," *Mol. Med. Today* 4:84–92 (Feb. 1998).

Yang, Y. et al., "MHC Class I–Restricted Cytotoxic T Lymphocytes to Viral Antigens Destroy Hepatocytes in Mice Infected with E1–Deleted Recombinant Adenoviruses," *Immunity* 1:433–442 (Aug. 1994).

\* cited by examiner

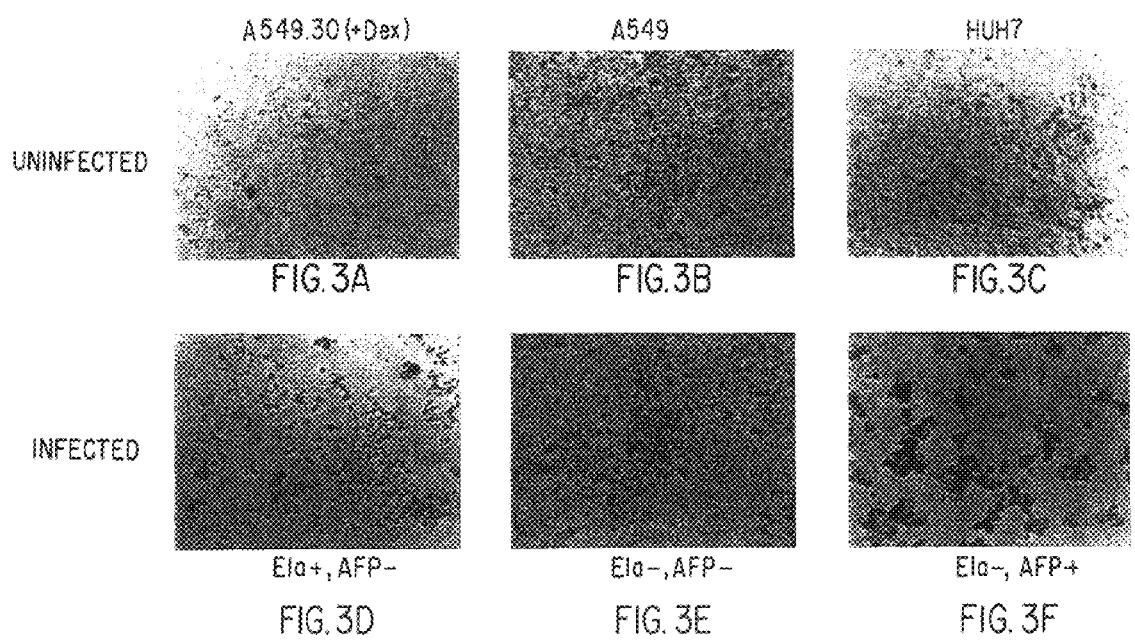

VECTORS FOR TISSUE-SPECIFIC REPLICATION

CROSS-REFERENCE TO RELATED APPLICATIONS

The present application is a continuation of U.S. application Ser. No. 08/849,117, filed Aug. 1, 1997, now U.S. Pat. No. 5,998,205, which is the U.S. National Phase of International Application No. PCT/US95/15455, filed Nov. 28, 1995, which is a continuation-in-part of U.S. application Ser. No. 08/487,992, filed Jun. 7, 1995 (now abandoned), which is a continuation-in-part of U.S. application Ser. No. 08/348,258, filed Nov. 28, 1994 (now abandoned).

BACKGROUND OF THE INVENTION

1. Field of the Invention

The invention generally relates to targeted gene therapy using recombinant vectors and particularly adenovirus vectors. The invention specifically relates to replication-conditional vectors and methods for using them. Such vectors are able to selectively replicate in a target tissue to provide a therapeutic benefit from the presence of the vector per se or from heterologous gene products expressed from the vector and distributed throughout the tissue. In such vectors, a gene essential for replication is placed under the control of a heterologous tissue-specific transcriptional regulatory sequence. Thus, replication is conditioned on the presence of a factor(s) that induces transcription or the absence of a factor(s) that inhibits transcription of the gene by means of the transcriptional regulatory sequence. With this vector, therefore, a target tissue can be selectively treated. The invention also relates to methods of using the vectors to screen a tissue for the presence or absence of transcriptional regulatory functions that permit vector replication by means of the transcriptional regulatory sequence. The invention also relates to cells for producing recombinant replication-conditional vectors useful for targeted gene therapy.

2. Background Art

Targeting Vectors

One of the major goals for therapeutic use of exogenous genes has been cell targeting with high specificity. General approaches have included systemic introduction of DNA, DNA-protein complexes, and liposomes. In situ administration of retroviruses has also been used for cells that are actively replicating.

However, because of the lack of, or significantly low, cell-specificity and inefficient gene transfer, the targeting of desired genes to specific cells in an organism has been a major obstacle for exogenous gene-based therapy. Thus, the use of such genes has been limited.

Tumor cells are among those cell types for which it would be especially desirable to provide a means for exogenous gene targeting. In an embodiment of the present invention, compositions and methods are provide to deliver exogenous genes to tumor cells safely and efficiently.

Adenoviruses Generally

Adenoviruses are nonenveloped, regular icosohedrons. The protein coat (capsid) is composed of 252 capsomeres of which 240 are hexons and 12 are pentons. Most of the detailed structural studies of the adenovirus polypeptides have been done for adenovirus types 2 and 5. The viral DNA is $23.85 \times 10^6$ daltons for adenovirus 2 and varies slightly in size depending on serotype. The DNA has inverted terminal repeats and the length of these varies with the serotype.

The replicative cycle is divided into early (E) and late (L) phases. The late phase defines the onset of viral DNA replication. Adenovirus structural proteins are generally synthesized during the late phase. Following adenovirus infection, host DNA and protein synthesis is inhibited in cells infected with most serotypes. The adenovirus lytic cycle with adenovirus 2 and adenovirus 5 is very efficient and results in approximately 10,000 virions per infected cell along with the synthesis of excess viral protein and DNA that is not incorporated into the virion. Early adenovirus transcription is a complicated sequence of interrelated biochemical events, but it entails essentially the synthesis of viral RNAs prior to the onset of viral DNA replication.

The organization of the adenovirus genome is similar in all of the adenovirus groups and specific functions are generally positioned at identical locations for each serotype studied. Early cytoplasmic messenger RNAs are complementary to four defined, noncontiguous regions on the viral DNA. These regions are designated (E1–E4). The early transcripts have been classified into an array of immediate early (E1a), delayed early (E1b, E2a, E2b, E3 and E4), and intermediate (IVa2.IX) regions.

The E1a region is involved in transcriptional transactivation of viral and cellular genes as well as transcriptional repression of other sequences. The E1a gene exerts an important control function on all of the other early adenovirus messenger RNAs. In normal tissues, in order to transcribe regions E1b, E2a, E2b, E3, or E4 efficiently, active E1a product is required. However, as discussed below, the E1a function may be bypassed. Cells may be manipulated to provide E1a-like functions or may naturally contain such functions. The virus may also be manipulated to bypass the functions as described below.

The E1b region is required for the normal progression of viral events late in infection. The E1b product acts in the host nucleus. Mutants generated within the E1b sequences exhibit diminished late viral mRNA accumulation as well as impairment in the inhibition of host cellular transport normally observed late in adenovirus infection (Berkner, K. L., *Biotechniques* 6:616–629 (1988)). E1b is required for altering functions of the host cell such that processing and transport are shifted in favor of viral late gene products. These products then result in viral packaging and release of virions. E1b produces a 19 kD protein that prevents apoptosis. E1b also produces a 55 kD protein that binds to p53.

For a complete review on adenoviruses and their replication, see Horwitz, M. S., *Virology* 2d ed., Fields, B. N., eds., Raven Press Limited, New York (1990), Chapter 60, pp. 1679–1721.

Adenovirus as Recombinant Delivery Vehicle

Adenovirus provides advantages as a vector for adequate gene delivery for the following reasons. It is a double stranded DNA nonenveloped virus with tropism for the human respiratory system and gastrointestinal tract. It causes a mild flu-like disease. Adenoviral vectors enter cells by receptor mediated endocytosis. The large (36 kilobase) genome allows for the removal of genes essential for replication and nonessential regions so that foreign DNA may be inserted and expressed from the viral genome. Adenoviruses infect a wide variety of cell types in vivo and in vitro. Adenoviruses have been used as vectors for gene therapy and for expression of heterologous genes. The expression of viral or foreign genes from the adenovirus genome does not require a replicating cell. Adenovirus vectors rarely integrate into the host chromosome; the adenovirus genome remains as an extrachromosomal element in the cellular nucleus. There is no association of human malignancy with adenovirus infection; attenuated strains have been developed and have been used in humans for live vaccines.

For a more detailed discussion of the use of adenovirus vectors for gene therapy, see Berkner, K. L., *Biotechniques* 6:616–629 (1988); Trapnell, B. C., *Advanced Drug Delivery Reviews* 12:185–199 (1993).

Adenovirus vectors are generally deleted in the E1 region of the virus. The E1 region may then be substituted with the DNA sequences of interest. It was pointed out in a recent article on human gene therapy, however, that "the main disadvantage in the use of adenovirus as a gene transfer vector is that the viral vector generally remains episomal and does not replicate, thus, cell division leads to the eventual loss of the vector from the daughter cells" (Morgan, R. A., et al., *Annual Review of Biochemistry* 62:191–217 (1993)) (emphasis added).

Non-replication of the vector leads not only to eventual loss of the vector without expression in most or all of the target cells but also leads to insufficient expression in the cells that do take up the vector, because copies of the gene whose expression is desired are insufficient for maximum effect. The insufficiency of gene expression is a general limitation of all non-replicating delivery vectors. Thus, it is desirable to introduce a vector that can provide multiple copies of a gene and hence greater amounts of the product of that gene. The present invention overcomes the disadvantages discussed above by providing a tissue-specific, and especially a tumor-specific replicating vector, multiple DNA copies, and thus increased amounts of gene product.

Production of Adenoviral Vectors

Adenoviral vectors for recombinant gene expression have been produced in the human embryonic kidney cell line 293 (Graham, F. L. et al., *J. Gen. Virol.* 36:59–72 (1977)). This cell line, initially transformed with human adenovirus 5, now contains the left end of the adenovirus 5 genome and expresses E1. Therefore, these cells are permissive for growth of adenovirus 2 and adenovirus 5 mutants defective in E1 functions. They have been extensively used for the isolation and propagation of E1 mutants. Therefore, 293 cells have been used for helper-independent cloning and expression of adenovirus vectors in mammalian cells. E1 genes integrated in cellular DNA of 293 cells are expressed at levels which permit deletion of these genes from the viral vector genome. The deletion provides a nonessential region into which DNA may be inserted. For a review, see, Young, C. S. H., et al. in *The Adenoviruses*, Ginsberg, H. S., ed., Plenum Press, New York and London (1984), pp. 125–172.

However, 293 cells are subject to severe limitations as producer cells for adenovirus vectors. Growth rates are low. Titres are limited, especially when the vector produces a heterologous gene product that proves toxic for the cells. Recombination with the viral E1 sequence in the genome can lead to the contamination of the recombinant defective virus with unsafe wild-type virus. The quality of certain viral preparations is poor with regard to the ratio of virus particle to plaque forming unit. Further, the cell line does not support growth of more highly deleted mutants because the expression of E1 in combination with other viral genes in the cellular genome (required to complement the further deletion), such as E4, is toxic to the cells. Therefore, the amount of heterologous DNA that can be inserted into the viral genome is limited in these cells. It is desirable, therefore, to produce adenovirus vectors for gene therapy in a cell that cannot produce wild-type recombinants and can produce high titres of high-equality virus. The present invention overcomes these limitations.

SUMMARY OF THE INVENTION

In view of the limitations discussed above, a general object of the invention is to provide novel vectors for tissue-specific vector replication and gene expression from the replicating vector. Accordingly, the invention is directed to a vector that contains a gene which is essential for replication, and which gene is operably linked to a heterologous transcriptional regulatory sequence, such that a vector is created whose replication is conditioned upon the presence of a trans-acting transcriptional regulatory factor(s) that permits transcription from the transcriptional regulatory sequence, or the absence of a transcriptional regulatory factor(s) that normally prevents transcription from that transcriptional regulatory sequence. Thus, these regulatory sequences are specifically activated or derepressed in the target tissue so that replication of the vector proceeds in that tissue.

Another object of the invention is to provide tissue-specific treatment of an abnormal tissue. Thus, a further object of the invention is to provide a method to selectively distribute a vector in vivo in a target tissue, such that a greater number of cells are treated than would be treated with a non-replicating vector, and treatment is avoided or significantly reduced in non-target tissue. Accordingly, a method is provided for selectively distributing a vector in a target tissue by introducing the replication-conditional vector of the present invention into a target tissue that contains a transcriptional regulatory factor(s) that allows replication of the vector or is deficient in a transcription-inhibiting factor(s) that prevents replication of the vector.

For providing tissue-specific treatment, another object of the invention is to selectively distribute a polynucleotide in a target tissue in vivo. Accordingly, the invention is directed to a method for selectively distributing a polynucleotide in a target tissue in vivo by introducing the replication-conditional vector of the present invention, containing the polynucleotide, into the target tissue that contains a transcriptional regulatory factor(s) that allows replication of the vector or is deficient in a transcription-inhibiting factor(s) that prevents replication of the vector.

For providing tissue-specific treatment, a another object of the invention is to selectively distribute a heterologous gene product in a target tissue. Accordingly, the replication-conditional vectors of the present invention are constructed so that they contain a heterologous DNA sequence encoding a gene product that is expressed in the vector. When the vector replicates in the target tissue, effective quantities of the desired gene product are also produced in the target tissue.

Another object of the invention is to provide a method to identify abnormal tissue that can be treated by the vectors of the present invention. Therefore, a further object of the invention is to identify a tissue in which the replication-conditional vectors of the present invention can be replicated by means of the transcriptional regulatory sequence contained on the vector. Accordingly, the invention is further directed to a method wherein the replication-conditional vectors of the present invention are exposed to a given abnormal tissue. If that tissue contains a transcriptional regulatory factor(s) that allows replication of the vector or is deficient in a transcription-inhibiting factor(s) that prevents replication of the vector, then replication of the vector will occur and can be detected. Following identification of such a tissue, targeted treatment of that tissue can be effected by tissue-specific transcription and the consequent vector replication in that tissue in vivo.

Thus, a method is provided for assaying vector utility for tissue treatment comprising the steps of removing a tissue biopsy from a patient, explanting the biopsy into tissue culture, introducing a replication-conditional vector into the cells of the biopsy, and assaying for vector replication in the cells.

Another object of the invention is to provide producer cell lines for vector production. Preferably, the cell lines have one or more of the following characteristics: high titer virus production, resistance to toxic effects due to heterologous gene products expressed in the vector, lack of production of wild-type virus contaminating the virus preparation and resulting from recombination between integrated viral sequences and vector sequences, growth to high density and in suspension, unlimited passage potential, high growth rate, and by permitting the growth of highly deleted viruses that are impaired for viral functions and able to accommodate large pieces of heterologous DNA.

Accordingly, in a further embodiment of the invention, a cell line is provided containing the replication-conditional vector of the present invention, the cells of which cell line contain a transcriptional regulatory factor(s) that allows replication of the vector or is deficient in a transcription-inhibiting factor(s) that prevents replication of the vector.

In further embodiments of the invention, the cell line contains nucleic acid copies of the replicated vector. In other embodiments, the cell line contains virions produced in the cell by replication in the cell of the replication-conditional vector.

In further embodiments, a method is provided for producing a replication-conditional vector or virion comprising the steps of culturing the producer cell line described above and recovering the vector or virion from the cells. In still further embodiments, a method is provided for producing replication-conditional virions free of wild-type virions or viral vectors free of wild-type vectors, comprising the steps of culturing the producer cell line described above and recovering the replication-deficient virions or vectors from the cells.

In a preferred methods of treatment and diagnosis, the tissue is abnormally proliferating, and especially is tumor tissue. However, the methods are also directed to other abnormal tissue as described herein.

In preferred embodiments of the invention, the replication-conditional vector is a DNA tumor viral vector. In a further preferred embodiment, the DNA tumor viral vector is a vector selected from the group consisting of herpesvirus, papovavirus, papillomavirus, parvovirus, and hepatitis virus vectors. In a most preferred embodiment, the vector is an adenovirus vector. However, it is to be understood that potentially any vector source is useful if it contains a gene essential for replication that can be operably linked to a tissue-specific transcriptional regulatory sequence.

In further methods of treatment and diagnosis, the vector is introduced into the tissue by infection.

Replication can be vector nucleic acid replication alone or can also include virus replication (i.e., virion production). Thus, either DNA or virions or both may be distributed in the target tissue.

In a further preferred embodiment of the invention, a gene in the adenovirus E1 region is operably linked to the tissue-specific transcriptional regulatory sequence. Preferably, the E1a or E1b gene is operably linked to the tissue-specific transcriptional regulatory sequence.

In a further embodiment of the invention, the vector encodes a heterologous gene product. This heterologous gene product is expressed from the vector replicating in the target tissue.

In a further embodiment of the methods of treatment, the heterologous gene product is toxic for the target tissue.

In a further embodiment of the methods, the heterologous gene product acts on a non-toxic prodrug, converting the non-toxic prodrug into a form that is toxic for the target tissue. Preferably, the toxin has anti-tumor activity or eliminates cell proliferation.

In preferred embodiments of the invention, the transcriptional regulatory sequence is a promoter. Preferred promoters include, but are not limited to, carcinoembryonic antigen (CEA), DE3, α-fetoprotein (AFP), Erb-B2, surfactant, and especially lung surfactant, and the tyrosinase promoter. However, any genetic control region that controls transcription of the essential gene can be used to activate (or derepress) the gene. Thus, other genetic control elements, such as enhancers, repressible sequences, and silencers, can be used to regulate replication of the vector in the target cell. The only requirement is that the genetic element be activated, derepressed, enhanced, or otherwise genetically regulated by factors in the host cell and, with respect to methods of treatment, not in the non-target cell.

Preferred enhancers include the DF3 breast cancer-specific enhancer and enhancers from viruses and the steroid receptor family. Other preferred transcriptional regulatory sequences include NF1, SP1, AP1, and FOS/JUN.

In further embodiments, promoters are not necessarily activated by factors in the target tissue, but are derepressed by factors present in the target tissue. Thus, in the target tissue, repression is lifted.

Transcriptional regulatory factors include, but are not limited to, transactivating factors produced by endogenous viral sequences such as from cytomegalovirus (CMV), HIV, Epstein-Barr virus (EBV), Herpes simplex virus (HSV), SV40, and other such viruses that are pathogenic in mammals and, particularly, in humans.

Methods for making such vectors are well known to the person of ordinary skill in the art. The art adequately teaches the construction of recombinant vectors with deletions or modifications in specific coding sequences and operable linkage to a heterologous transcription control sequence such that expression of a desired coding region is under control of the heterologous transcriptional regulatory sequence. Many viral sequences have been adequately mapped such that it is routine to identify a gene of choice and use appropriate well known techniques (such as homologous recombination of the virus with deleted or otherwise modified plasmids) to construct the vectors for tissue-specific replication and expression.

BRIEF DESCRIPTION OF THE FIGURES

FIGS. 2(A–C). PCR identification of recombinant adenovirus with E1a expressed from the hepatoma-specific AFP promoter. FIG. 2A shows that viral plaques are produced by viral genomes containing the AFP promoter operably linked to E1a.

FIGS. 3(A–F). Tissue specific adenovirus with E1a expressed from the AFP promoter. The experiment shows cytopathic effects and spreading of cell death following infection with the virus AVAFPE1a. FIGS. 3A–3C show uninfected controls in A549.30, A549, and HuH 7 cells, respectively. FIGS. 3D–3F show the results of infection with the virus in A549.30, A549, and HuH 7 cells, respectively.

DETAILED DESCRIPTION OF THE PREFERRED EMBODIMENTS

Definitions

Figure 1A:
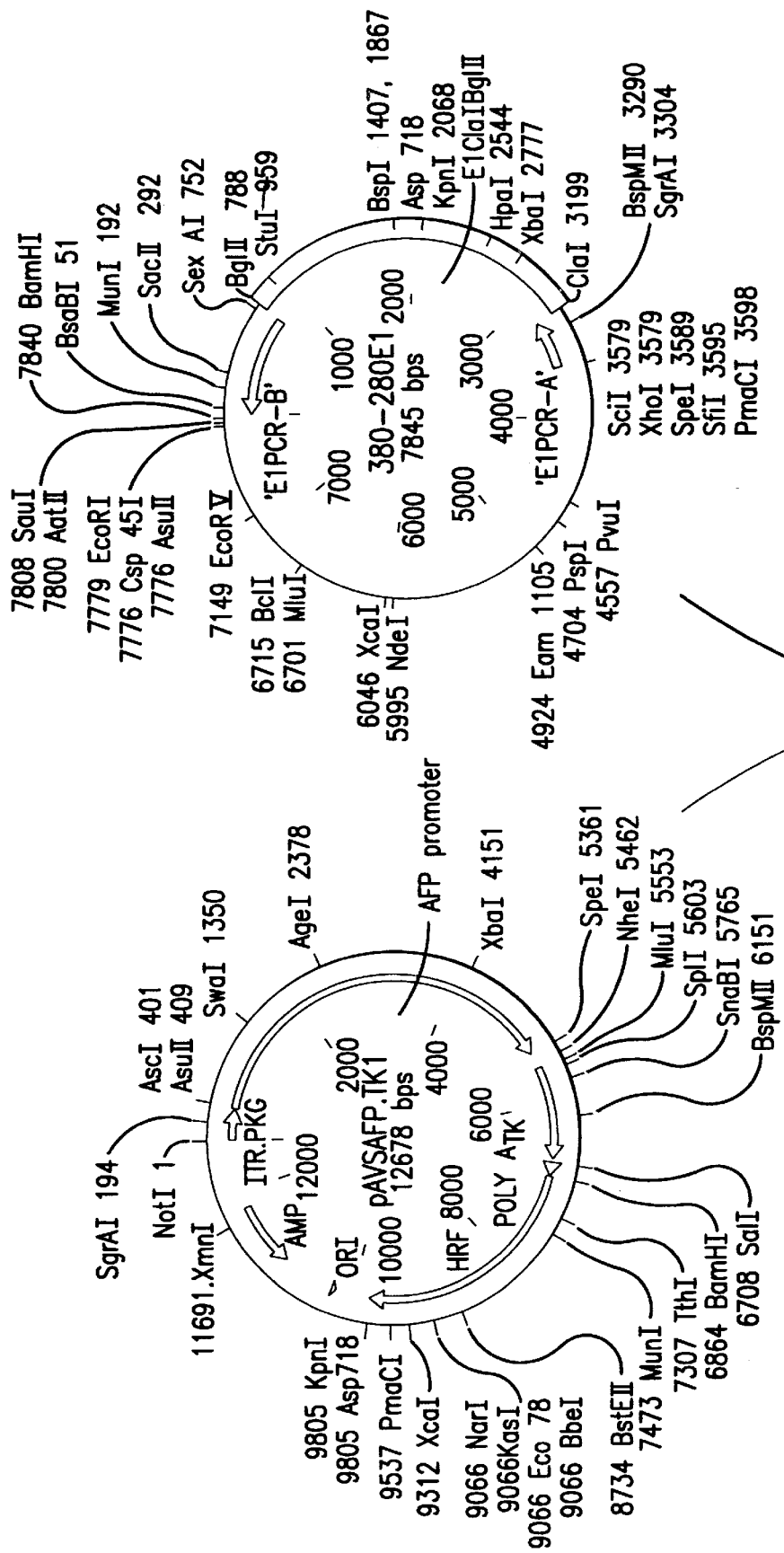
FIG. 1A-B. Cloning of pAVE1a02i: pAVSAFP.TK1 was digested with NheI/MunI. A 10667 bp fragment was isolated. 380–280E1 was digested with SpeI/MunI. A 3397 bp fragment was isolated. The isolated fragments were ligated to form pAVE1a02i.

The term "abnormally proliferating" is intended to mean a cell having a higher mitotic index than its normally-functioning counterpart, such that there is an abnormal accumulation of such cells.

The term "anti-tumor activity" is intended to mean any activity which inhibits, prevents, or destroys the growth of a tumor.

The term "distributing" is intended to mean the spreading of a vector and its attendant heterologous gene (product) (when present on the vector) throughout a target tissue, and especially throughout abnormally proliferating tissue (non-malignant or malignant). The object of the distribution is to deliver the vector, gene product or the effects of the gene product (as by a bystander effect, for example) to substantially all or a significant number of cells of the target tissue, so as to treat substantially the entire target tissue.

The term "enhancer" is used according to its art-recognized meaning. It is intended to mean a sequence found in eukaryotes and certain eukaryotic viruses which can increase transcription from a gene when located (in either orientation) up to several kilobases from the gene being studied. These sequences usually act as enhancers when on the 5' side (upstream) of the gene in question. However, some enhancers are active when placed on the 3' side (downstream) of the gene. In some cases, enhancer elements can activate transcription from a gene with no (known) promoter.

The term "functional inactivation" is intended to mean a genetic lesion that prevents the normal activity of a gene product. Thus, functional inactivation could result from a mutation in the gene encoding the gene product. Such a lesion includes insertions, deletions, and base changes. Alternatively, functional inactivation may occur by the abnormal interaction of the normal gene product with one or more other cellular gene products which bind to or otherwise prevent the functional activity of said gene product. Thus, the gene product may be a protein produced from a normal gene but which cannot perform its ordinary and normal function because of an interaction with a second factor.

The term "gene essential for replication" refers to a genetic sequence whose transcription is required for the vector to replicate in the target cell.

The term "gene product" is intended to mean DNA, RNA, protein, peptides, or viral particles. Thus, the distribution, for the purposes of the invention, is of any of these components.

The term "heterologous" means a DNA sequence not found in the native vector genome. With respect to a "heterologous transcriptional regulatory sequence", "heterologous" indicates that the transcriptional regulatory sequence is not naturally ligated to the DNA sequence for the gene essential for replication of the vector.

The term "promoter" is used according to its art-recognized meaning. It is intended to mean the DNA region, usually upstream to the coding sequence of a gene or operon, which binds RNA polymerase and directs the enzyme to the correct transcriptional start site.

The term "replication" means duplication of a vector. This duplication, in the case of viruses, can occur at the level of nucleic acid, or at the level of infectious viral particle. In the case of DNA viruses, replication at the nucleic acid level is DNA replication. In the case of RNA viruses, nucleic acid replication is replication into plus or minus strand (or both). In the case if retroviruses, replication at the nucleic acid level includes the production of cDNA as well as the further production of RNA viral genomes. The essential feature is nucleic acid copies of the original viral vector. However, replication also includes the formation of infectious DNA or RNA viral particles. Such particles may successively infect cells in a given target tissue thus distributing the vector through all or a significant portion of the target tissue.

The term "replication-conditional vector" refers to a vector which when introduced into a tissue will not replicate unless a transcriptional regulatory sequence in that vector is activated or derepressed in that tissue. That is, replication depends upon transcription by means of that transcriptional regulatory sequence. Such a vector is replication-conditional as described because it has been modified in the following manner. A gene that is essential for replication has been modified by replacing the transcriptional regulatory sequence on which transcription of that gene normally depends with a heterologous transcriptional regulatory sequence. This transcriptional regulatory sequence depends upon the presence of transcriptional regulatory factors or the absence of transcriptional regulatory inhibitors. The presence of these factors in a given tissue or the absence of such inhibitors in a given tissue provides the replication conditionality. Accordingly, the native transcriptional regulatory sequence may be replaced with the heterologous transcriptional regulatory sequence. Alternatively, the native transcriptional regulatory sequence may be disabled or rendered dysfunctional by partial removal (deletion) or other mutation (one or more base changes, insertions, inversions, etc.).

The gene sequence may be a coding sequence. It may contain one or more open reading frames, as well as intron sequences. However, such a sequence is not limited to a coding sequence, but includes sequences that are transcribed into RNA, which RNA is itself essential for vector replication. The essential feature is that the transcription of the gene sequences does not depend on the native transcriptional regulatory sequences.

The term "silencer," used in its art-recognized sense, means a sequence found in eucaryotic viruses and eucaryotes which can decrease or silence transcription of a gene when located within several kilobases of that gene.

The term "tissue-specific" is intended to mean that the transcriptional regulatory sequence to which the gene essential for replication is operably linked functions specifically in that tissue so that replication proceeds in that tissue. This can occur by the presence in that tissue, and not in non-target tissues, of positive transcription factors that activate the transcriptional regulatory sequence. It can also occur by the absence of transcription inhibiting factors that normally occur in non-target tissues and prevent transcription as a result of the transcription regulatory sequence. Thus, when transcription occurs, it proceeds into the gene essential for replication such that in that target tissue, replication of the vector and its attendant functions occur.

As described herein, tissue specificity is particularly relevant in the treatment of the abnormal counterpart of a normal tissue. Such counterparts include, but are not limited to, liver tissue and liver cancer, breast tissue and breast cancer, melanoma and normal skin tissue. Tissue specificity also includes the presence of an abnormal tissue type interspersed with normal tissue of a different tissue type, as for example in the case of metastases of colon cancer, breast cancer, and the like, into tissue such as liver. In this case, the target tissue is the abnormal tissue, and tissue specificity reflects the restriction of vector replication to the abnormal tissue interspersed in the normal tissue. It is also to be understood that tissue specificity, in the context of treatment, is particularly relevant in vivo. However, as described herein, ex vivo treatment and tissue replacement also falls within the concept of tissue specificity according to the present invention.

The term "transcriptional regulatory function" or "transcriptional regulatory factor" is intended to mean any cellular function whose presence activates the heterologous transcriptional regulatory sequence described herein or whose absence permits transcription as a result of the transcriptional regulatory sequences described herein. It is understood that in the given target tissue, a tissue that "lacks the transcriptional regulatory factor" or is "deficient" in the transcriptional regulatory factor could refer to either the absence of the factor or the functional inactivation of the factor in the target tissue.

The term "transcriptional regulatory sequence" is used according to its art-recognized meaning. It is intended to mean any DNA sequence which can, by virtue of its sequence, cause the linked gene to be either up- or down-regulated in a particular cell. In one embodiment of the present invention, the native transcriptional regulatory sequence is completely deleted from the vector and replaced with a heterologous transcriptional regulatory sequence. The transcriptional regulatory sequence may be adjacent to the coding region for the gene that is essential for replication, or may be removed from it. Accordingly, in the case of a promoter, the promoter will generally be adjacent to the coding region. In the case of an enhancer, however, an enhancer can be found at some distance from the coding region such that there is an intervening DNA sequence between the enhancer and the coding region. In some cases, the native transcriptional regulatory sequence remains on the vector but is non-functional with respect to transcription of the gene essential for replication.

Various combinations of transcriptional regulatory sequences can be included in a vector. One or more may be heterologous. Further, one or more may have the tissue-specificity. For example, a single transcriptional regulatory sequence could be used to drive replication by more than one gene essential for replication. This is the case, for example, when the gene product of one of the genes drives transcription of the further gene(s). An example is a heterologous promoter linked to a cassette containing an E1a coding sequence (E1a promoter deleted) and the entire E1b gene. In such a cascade, only one heterologous transcriptional regulatory sequence may be necessary. When genes are individually (separately) controlled, however, more than one transcriptional regulatory sequence can be used if more than one such gene is desired to control replication.

The vectors of the present invention, therefore, also include transcriptional regulatory sequence combinations wherein there is more than one heterologous transcriptional regulatory sequence, but wherein one or more of these is not tissue-specific. For example, one transcriptional regulatory sequence can be a basal level constitutive transcriptional regulatory sequence. For example, a tissue-specific enhancer can be combined with a basal level constitutive promoter.

Vectors

The preferred vectors of the present invention are adenoviral vectors. In a preferred embodiment of the invention, an adenovirus vector contains a tissue-specific transcriptional regulatory sequence linked to a gene in the E1 region.

In one embodiment, both E1a and E1b are operably linked to heterologous tissue-specific transcriptional regulatory sequences. In an alternative embodiment, only E1a is linked; E1b remains intact. In still another embodiment, E1b is linked, and E1a remains intact or is deleted. In any case, one or more tissue-specific and promoter-specific cellular transcriptional regulatory factors allows virus replication to proceed by transcribing the E1a and/or E1b gene functionally linked to the promoter. Further, either one or both of the E1b functions may be linked to the transcriptional regulatory sequence.

In alternative embodiments, adenovirus vectors are provided with any of the other genes essential for replication, such as E2–E4, under control of a heterologous transcriptional regulatory sequence.

The invention further embodies the use of plasmids and vectors having only the essential regions of adenovirus needed for replication with either E1a, E1b 19 kDa gene, or E1b 55 kDa gene, or some combination thereof, modified. Such a plasmid, lacking any structural genes, would be able to undergo DNA replication. Accordingly, the vectors of the invention may consist essentially of the transcriptional regulatory sequence and one or more genes essential for replication of the vector. In the case of viral vectors, the vectors may consist essentially of the transcriptional regulatory sequence and the gene or genes essential for replication or life-cycle functions of the virus. It is also understood that these vectors may also further consist essentially of a DNA sequence encoding one or more toxic heterologous gene products when such vectors are intended as expression vectors for treatment.

In broader embodiments, the vector is derived from another DNA tumor virus. Such viruses generally include, but are not limited to, Herpesviruses (such as Epstein-Barr virus, cytomegalovirus, *Herpes zoster*, and *Herpes simplex*), papillomaviruses, papovaviruses (such as polyoma and SV40), and hepatitis viruses.

The alternative viruses preferably are selected from any group of viruses in which the essential genes for replication of the virus can be placed under the control of a tissue-specific transcriptional regulatory sequence. All serotypes are included. The only common property of such viruses, therefore, is that they are transducible into target tissue, are genetically manipulatable, and are non-toxic when not replicating.

The relevant viral gene(s) are those that are essential for replication of the viral vector or of the virus. Examples of genes include, but are not limited to, the E6 and E7 regions of human papilloma virus, 16 and 18, T antigen of SV40, and CMV immediate early genes, polymerases from retroviruses and the like. Essentially, these include any gene that is necessary for the life cycle of the virus.

In further embodiments, the vector is derived from an RNA virus. In still further embodiments, the vector is derived from a retrovirus. It is understood, however, that potentially any replicating vector can be made and used according to the essential design disclosed herein.

The vectors described herein can be constructed using standard molecular biological techniques. Standard techniques for the construction of such vectors are well-known to those of ordinary skill in the art, and can be found in references such as Sambrook et al., in *Molecular Cloning: A Laboratory Manual*, Cold Spring Harbor, N.Y. (1989), or any of the myriad of laboratory manuals on recombinant DNA technology that are widely available. A variety of strategies are available for ligating fragments of DNA, the choice of which depends on the nature of the termini of the DNA fragments and can be readily determined by the skilled artisan.

An adenovirus vector, in a preferred embodiment, is constructed first by constructing, according to standard techniques, a shuttle plasmid which contains, beginning at the 5' end, the "critical left end elements," which include an adenoviral 5' ITR, an adenoviral encapsidation signal, and an E1a enhancer sequence; a promoter (which may be an adenoviral promoter or a foreign promoter); a tripartite leader sequence, a multiple cloning site (which may be as herein described); a poly A signal; and a DNA segment which corresponds to a segment of the adenoviral genome. Such DNA segment serves as a substrate for homologous recombination with a modified or mutated adenovirus. The plasmid may also include a selectable marker and an origin of replication. The origin of replication may be a bacterial origin of replication. Representative examples of such shuttle plasmids include pAVS6, as discussed herein and see Trapnell, B. et al., *Adv. Drug Deliv. Rev* 12:185–189 (1994). A desired DNA sequence containing a heterologous gene may then be inserted into the multiple cloning site to produce a plasmid vector.

This construct then is used to produce an adenoviral vector. Homologous recombination then is effected with a modified or mutated adenovirus in which one or more of the native transcriptional regulatory sequences have been deleted and replaced with the desired transcriptional regulatory sequence. Such homologous recombination may be effected through co-transfection of the plasmid vector and the modified adenovirus into a helper cell line by $CaPO_4$ precipitation.

Through such homologous recombination, a vector is formed which includes adenoviral DNA free of one or more of the native transcriptional regulatory sequences. This vector may then be transfected into a helper cell line for viral replication and to generate infectious viral particles. Transfections may take place by electroporation, calcium phosphate precipitation, microinjection, or through proteoliposomes.

The vector may include a multiple cloning site to facilitate the insertion of DNA sequence(s) containing the heterologous gene into the cloning vector. In general, the multiple cloning site includes "rare" restriction enzyme sites; i.e., sites which are found in eukaryotic genes at a frequency of from about one in every 10,000 to about one in every 100,000 base pairs. An appropriate vector is thus formed by cutting the cloning vector by standard techniques at appropriate restriction sites in the multiple cloning site, and then ligating the DNA sequence containing the heterologous gene into the cloning vector.

The DNA sequence encoding the heterologous gene product is under the control of a suitable promoter. Suitable promoters which may be employed include, but are not limited to, adenoviral promoters, such as the adenoviral major late promoter; or heterologous promoters, such as the cytomegalovirus promoter; the Rous sarcoma virus promoter; inducible promoters, such as the mouse mammary tumor virus (MMTV) promoter, the metallothionein promoter; heat shock promoters; the albumin promoter; the ApoE promoter; and the ApoAI promoter. It is to be understood, however, the scope of the present invention is not limited to specific foreign genes or promoters.

In one embodiment, the adenovirus may be constructed by using a yeast artificial chromosome containing an adenoviral genome according to the method described in Ketner, et al., *Proc. Nat. Acad. Sci.* 91:6186–6190 (1994), in conjunction with the teachings contained herein. In this embodiment, the adenovirus yeast artificial chromosome is produced by homologous recombination in vivo between adenoviral DNA and yeast artificial chromosome plasmid vectors carrying segments of the adenoviral left and right genomic termini. A DNA sequence containing the heterologous gene then may be cloned into the adenoviral DNA. The modified adenoviral genome then is excised from the adenovirus yeast artificial chromosome in order to be used to generate infectious adenoviral particles.

The infectious viral particles may then be administered in vivo to a host. The host may be an animal host, including mammalian, non-human primate, and human hosts.

The viral particles may be administered in combination with a pharmaceutically acceptable carrier suitable for administration to a patient. The carrier may be a liquid carrier (for example, a saline solution), or a solid carrier, such as, for example, microcarrier beads.

Treatment

In preferred embodiments, the methods are specifically directed to the introduction into a target tissue of a replication-conditional adenoviral vector. This vector selectively replicates in the cells of the target tissue. The replication is conditioned upon the function of a transcriptional regulatory sequence to which a viral gene is operably linked, which gene is necessary for vector replication. Thus, in the target tissue, replication can occur because either a cellular function in the target tissue allows transcription. Alternatively, there is a deficiency in a cellular function in the target tissue that normally prevents or inhibits transcription. The presence or absence of such functions provides the selectivity that allows the treatment of a specific tissue with minimum effect on the surrounding tissue(s).

The present invention thus provides methods for selectively distributing a polynucleotide in a given tissue in vivo, significantly reducing or avoiding distribution in non-target tissue. The polynucleotide is provided in the replication-conditional vector which is selectively distributed in the given tissue.

The present invention also provides methods for selectively expressing a gene product in a given tissue, avoiding or significantly reducing expression in non-target or non-tumor tissue. The invention provides methods for distribution of the above-mentioned to a greater number of target cells than would be reached using a non-replicating vector. Successive infection provides a "domino effect" so that all or substantially all of the cells in the target tissue is reached. Cells in addition to those first exposed to the polynucleotide, vector, or gene product, are thus potentially reached by the methods.

Such treatment is particularly necessary in cases in which surgical intervention is not feasible. For example, in patients with abnormal tissue intimately associated with neural tissue, surgery may be precluded or highly dangerous. Further, in the case of multiple metastases or microscopic metastases, surgery is not feasible.

In the target tissue, DNA replication alone may occur. Late viral functions that result in packaging of vector DNA into virions may also occur.

The vector may be introduced into the target tissue as naked DNA or by means of encapsidation (as an infectious virus particle or virion). In the latter case, the distribution is accomplished by successive infections of cells in the tissue by the virus such that substantially all or a significant number of the daughter cells are infected.

Tissue specificity is particularly relevant with respect to targeting an abnormal counterpart of a particular tissue type while avoiding the normal counterpart of the tissue, or avoiding surrounding tissue of a different type than the abnormal tissue, while treating the abnormal tissue. For example, the vectors of the present invention are useful for treating metastases to the liver. One specific example is colon cancer, which often metastasizes into the liver. It has been found that even when colon cancer metastasizes into the liver, the CEA promoter is active in the cells of the metastases but not in normal liver cells. Accordingly, normal human adult liver should not support replication of a virus that has viral genes essential for replication linked to the colon cancer CEA-specific promoter. Replication should occur in the primary cancer cells. Another example is breast cancer, which also metastasizes to the liver. In this case, the DF3 mucin enhancer is linked to a gene essential for replication such as both E1a and E2a. Replication should occur in breast cancer but not in normal liver. A further example is the α-fetoprotein promoter, which is active in hepatocellular carcinoma. This promoter is linked to a gene essential for replication. It has been found that the promoter is active only in the hepatocellular carcinoma. Accordingly, a virus is used that has a gene essential for replication linked to this promoter. Replication should be limited to hepatocellular carcinoma. A further example is the tyrosinase promoter. This promoter is linked to a gene essential for replication. Replication should occur in melanoma and not in normal skin. In each case, replication is expected in the abnormal but not the normal cells.

In a further embodiment of the invention, the vector encodes a heterologous gene product which is expressed from the vector in the tissue cells. The heterologous gene product can be toxic for the cells in the targeted tissue or confer another desired property.

A gene product produced by the vector can be distributed throughout the tissue, because the vector itself is distributed throughout the tissue. Alternatively, although the expression of the gene product may be localized, its effect may be more far-reaching because of a bystander effect or the production of molecules which have long-range effects such as chemokines. The gene product can be RNA, such as antisense RNA or ribozyme, or protein. Examples of toxic products include, but are not limited to, thymidine kinase in conjunction with ganciclovir.

A wide range of toxic effects is possible. Toxic effects can be direct or indirect. Indirect effects may result from the conversion of a prodrug into a directly toxic drug. For example, Herpes simplex virus thymidine kinase phosphorylates ganciclovir to produce the nucleotide toxin ganciclovir phosphate. This compound functions as a chain terminator and DNA polymerase inhibitor, prevents DNA synthesis, and thus is cytotoxic. Another example is the use of cytosine deaminase to convert 5'-fluorocytosine to the anti-cancer drug 5'-fluorouracil. For a discussion of such "suicide" genes, see Blaese, R. M. et al., *Eur. J. Cancer* 30A:1190–1193 (1994).

Direct toxins include, but are not limited to, diphtheria toxin (Brietman et al., *Mol. Cell Bio.* 10:474–479 (1990)), pseudomonas toxin, cytokines (Blankenstein, T., et al., *J. Exp. Med.* 173:1047–1052 (1991), Colombo, M. P., et al., *J. Exp. Med.* 173:889–897 (1991), Leone, A., et al., *Cell* 65:25–35 (1991)), antisense RNAs and ribozymes (Zaia, J. A. et al., *Ann. N.Y. Acad. Sci.* 660:95–106 (1992)), tumor vaccination genes, and DNA encoding for ribozymes.

In accordance with the present invention, the agent which is capable of providing for the inhibition, prevention, or destruction of the growth of the target tissue or tumor cells upon expression of such agent can be a negative selective marker; i.e., a material which in combination with a chemotherapeutic or interaction agent inhibits, prevents or destroys the growth of the target cells.

Thus, upon introduction to the cells of the negative selective marker, an interaction agent is administered to the host. The interaction agent interacts with the negative selective marker to prevent, inhibit, or destroy the growth of the target cells.

Negative selective markers which may be used include, but are not limited to, thymidine kinase and cytosine deaminase. In one embodiment, the negative selective marker is a viral thymidine kinase selected from the group consisting of Herpes simplex virus thymidine kinase, cytomegalovirus thymidine kinase, and varicella-zoster virus thymidine kinase. When viral thymidine kinases are employed, the interaction or chemotherapeutic agent preferably is a nucleoside analogue, for example, one selected from the group consisting of ganciclovir, acyclovir, and 1–2-deoxy-2-fluoro-β-D-arabinofuranosil-5-iodouracil (FIAU). Such interaction agents are utilized efficiently by the viral thymidine kinases as substrates, and such interaction agents thus are incorporated lethally into the DNA of the tumor cells expressing the viral thymidine kinases, thereby resulting in the death of the target cells.

When cytosine deaminase is the negative selective marker, a preferred interaction agent is 5-fluorocytosine. Cytosine deaminase converts 5-fluorocytosine to 5-fluorouracil, which is highly cytotoxic. Thus, the target cells which express the cytosine deaminase gene convert the 5-fluorocytosine to 5-fluorouracil and are killed.

The interaction agent is administered in an amount effective to inhibit, prevent, or destroy the growth of the target cells. For example, the interaction agent is administered in an amount based on body weight and on overall toxicity to a patient. The interaction agent preferably is administered systemically, such as, for example, by intravenous administration, by parenteral administration, by intraperitoneal administration, or by intramuscular administration.

When the vectors of the present invention induce a negative selective marker and are administered to a tissue or tumor in vivo, a "bystander effect" may result, i.e., cells which were not originally transduced with the nucleic acid sequence encoding the negative selective marker may be killed upon administration of the interaction agent. Although the scope of the present invention is not intended to be limited by any theoretical reasoning, the transduced cells may be producing a diffusible form of the negative selective marker that either acts extracellularly upon the interaction agent, or is taken up by adjacent, non-target cells, which then become susceptible to the action of the interaction agent. It also is possible that one or both of the negative selective marker and the interaction agent are communicated between target cells.

In one embodiment, the agent which provides for the inhibition, prevention, or destruction of the growth of the tumor cells is a cytokine. In one embodiment, the cytokine is an interleukin. Other cytokines which may be employed include interferons and colony-stimulating factors, such as GM-CSF. Interleukins include, but are not limited to, interleukin-1, interleukin-1β, and interleukins-2–15. In one embodiment, the interleukin is interleukin-2.

In a preferred embodiment of the invention, the target tissue is abnormally proliferating, and preferably tumor tissue. The vector or virus is distributed throughout the tissue or tumor mass.

All tumors are potentially amenable to treatment with the methods of the invention. Tumor types include, but are not limited to hematopoietic, pancreatic, neurologic, hepatic, gastrointestinal tract, endocrine, biliary tract, sinopulmonary, head and neck, soft tissue sarcoma and carcinoma, dermatologic, reproductive tract, and the like. Preferred tumors for treatment are those with a high mitotic index relative to normal tissue. Preferred tumors are solid tumors, and especially, tumors of the brain, most preferably glioma.

The methods can also be used to target other abnormal cells, for example, any cells in which are harmful or otherwise unwanted in vivo. Broad examples include cells causing autoimmune disease, restenosis, and scar tissue formation.

Further, treatment can be ex vivo. Ex vivo transduction of tumor cells would overcome many of the problems with current viral delivery systems. Tissue is harvested under sterile conditions, dissociated mechanically and/or enzymatically and cultured under sterile conditions in appropriate media Vector preparations demonstrated to be free of endotoxins and bacterial contamination are used to transduce cells under sterile conditions in vitro using standard protocols. The accessibility of virus to cells in culture is currently superior to in vivo injection and permits introduction of vector viral sequences into essentially all cells. Following removal of virus-containing media cells are immediately returned to the patient or are maintained for several days in culture while testing for function or sterility is performed.

For example, patients with hypercholesterolemia have been treated successfully by removing portions of the liver, explanting the hepatocytes in culture, genetically modifying them by exposure to retrovirus, and re-infusing the corrected cells into the liver (Grossman et al., 1994).

Viral transduction also has potential applications in the area of experimental medicine. Transient expression of biological modifiers of immune system function such as IL-2, IFN-γ, GM-CSF or the B7 co-stimulatory protein has been proposed as a potential means of inducing anti-tumor responses in cancer patients.

In broader embodiments, the vector is derived from another DNA tumor virus. Such viruses generally include, but are not limited to, Herpesviruses (such as Epstein-Barr virus, cytomegalovirus, *Herpes zoster*, and *Herpes simplex*), papillomaviruses, papovaviruses (such as polyoma and SV40), and hepatitis viruses.

The relevant viral gene(s) are those that are essential for replication of the viral vector or of the virus. Examples of genes include, but are not limited to, the E6 and E7 regions of human papilloma virus, 16 and 18, T antigen of SV40, and CMV immediate early genes, polymerases from retroviruses and the like. Essentially, these include any gene that is necessary for the life cycle of the virus.

In further embodiments, the vector is derived from an RNA virus. In still further embodiments, the vector is derived from a retrovirus. It is understood, however, that potentially any replicating vector can be made and used according to the essential design disclosed herein.

Diagnostic

It is important to know whether the vectors of the invention will replicate in a specific tissue from a patient. If vector replication is found to be beneficial for therapy, then a screen is provided for those patients who best respond to the therapy disclosed herein. If it is found to be harmful, then there is a screen for prevention of the treatment of patients who would have an adverse response to the treatment. Currently, the only non-biological assays that are commonly used are expression screening, PCR, and sequencing. These often result in false negatives, are time-consuming, expensive, and yield only information in the best of cases about the status of the genes and not their biological function.

Accordingly, a method is provided for identifying an abnormal tissue, the cells of which contain a transcription factor that allows replication of a replication-conditional vector, or are deficient for an inhibitory factor for transcription.

In this method, a tissue biopsy is explanted, a replication-conditional vector is introduced into the cells of the biopsy, and vector DNA replication in the cells is quantitated. Accordingly, a method is provided for screening tissue for the presence of factors that allow vector replication, or for a deficiency of a factor that inhibits transcription. Such a screen is useful, among other things, for identifying tissue, prior to treatment, which will be amenable to treatment with a particular vector to be replicated in the tissue.

Therefore, a method is provided for assaying vector utility for treatment by removing a tissue biopsy from a patient, explanting the biopsy into tissue culture, introducing the replication-conditional vector into the biopsy, and assaying vector replication in the cells of the biopsy.

Testing or screening of tissues includes an assay for vector nucleic acid replication or for virus replication, when the vector is capable of forming infectious virions.

Thus, the invention provides a method for screening a tumor for transcription regulatory functions that allow vector replication or for the absence of these functions which would normally prevent the replication of a virus vector.

However, any abnormal tissue can be screened for the functions described above by an assay for nucleic acid or virus replication.

Producer Cells

In a further embodiment of the invention, a cell is provided which contains a virion produced in the cell by replication in the cell of the replication-conditional vectors of the present invention. Thus, the invention provides "producer cells" for the efficient and safe production of recombinant replication-conditional vectors for further use for targeted gene therapy in vivo.

One of the major problems with the currently available producer cells is that such cells contain, in the genome, viral sequences that provide complementing functions for the replicating vector. Because the cell contains such sequences, homologous recombination can occur between the viral sequence in the genome and the viral vector sequences. Such recombination can regenerate recombinant wild-type viruses which contaminate the vector or virus preparation produced in the producer cell. Such contamination is undesirable, as the wild-type viruses or vectors can then replicate in non-target tissue and thereby impair or kill non-target cells. Therefore, one of the primary advantages of the producer cells of the present invention is that they do not contain endogenous viral sequences homologous to sequences found in the vector to be replicated in the cells. The absence of such sequences avoids homologous recombination and the production of wild-type viral recombinants that can affect non-target tissue.

Accordingly, the invention embodies methods for constructing and producing replication-conditional virions in a cell comprising introducing the replication-conditional vector of the present invention into the cell wherein the genome of the cell is devoid of vector sequences, replicating the vector in the cell, forming the virion, and purifying the virion from the cell. Preferred vectors are DNA viral vectors, including but not limited to herpesvirus, papillomavirus, hepatitis virus, and papovavirus vectors. In preferred embodiments of the invention, the virion is an adenoviral virion and the vector is an adenoviral vector. In further embodiments of the invention, the cell is a tumor cell.

In a further preferred embodiment, the vector encodes a heterologous gene product such that the virion also encodes the gene product, and when the vector or virion are used for gene therapy, the therapy is facilitated by expression of the heterologous gene product. Alternatively, the producer cell can be used for the production of a heterologous gene product per se encoded by the vector. When the vector replicates in the producer cell, the gene product is expressed from the multiple copies of the gene encoding the gene product. Following expression, the gene product can be purified from the producer cells by conventional lysis procedures, or secreted from the producer cell by appropriate secretion signals linked to the heterologous gene by known methods. The transduction of cells by adenoviral vectors has been described. Transfection of plasmid DNA into cells by calcium phosphate (Hanahan, D., *J. Mol. Biol.* 166:577 (1983)), lipofection (Feigner et al., *PNAS* 84:7413 (1987)), or electroporation (Seed, B., *Nature* 329:840 ( )) has been described. DNA, RNA, and virus purification procedures are described (Graham et al., *J. Gen. Virol.* 36:59–72 (1977).

Preferred hosts for producer cell lines include but are not limited to HuH7, SW480, BIGF10, HepG2, MCF-7, and SK-MEL2. Primary tumors from which cell lines can be derived, or existing cell lines, can be tested for the ability to allow replication by means of the tissue-specific transcriptional regulatory sequence. Any primary tumor could be explanted and developed into producer cells for the vectors of the present invention. As long as the cell does not contain endogenous vector or viral sequences that could recombine with the vector or virus to produce wild-type vector or virus, the cell is potentially useful as a host. It is understood that any cell is potentially useful, not only tumor cells.

The ultimate goal for a producer cell line, and particularly an adenoviral producer line, is to produce the highest yield of vector with the least possibility of contamination by wild-type vector. Yield depends upon the number of cells infected. Thus, the more cells that it is possible to grow and infect, the more virus it is possible to generate. Accordingly, candidate cells would have a high growth rate and will grow to a high density. The cell should also have a high amount of viral receptor so that the virus can easily infect the cell. Another characteristic is the quality of the vector produced (i.e., the preparation should not include a high amount of non-infectious viral particles). Accordingly, candidate producer cells would have a low particle-to-plaque-forming-unit ratio. Thus, these cells are a preferred cell type for deriving a producer cell line. Primary explants or the known cell lines can be used.

Thus, such obtainable cells can serve as producer cells for recombinant replication-conditional vectors, viruses, and gene products.

Introduction of Vectors into Cells

A variety of ways have been developed to introduce vectors into cells in culture, and into cells and tissues of an animal or a human patient. Methods for introducing vectors into mammalian and other animal cells include calcium phosphate transfection, the DEAE-dextran technique, microinjection, liposome mediated techniques, cationic lipid-based techniques, transfection using polybrene, protoplast fusion techniques, electroporation and others. These techniques are well known to those of skill, are described in many readily available publications and have been extensively reviewed. Some of the techniques are reviewed in *Transcription and Translation, A Practical Approach*, Hames, B. D. and Higgins, S. J., eds., IRL Press, Oxford (1984), herein incorporated by reference in its entirety, and *Molecular Cloning*, Second Edition, Maniatis et al., Cold Spring Harbor Laboratory Press, Cold Spring Harbor, N.Y. (1989), herein incorporated by reference in its entirety.

Several of these techniques have been used to introduce vectors into tissues and cells in animals and human patients. Chief among these have been systemic administration and direct injection into sites in situ. Depending on the route of administration and the vector, the techniques have been used to introduce naked DNA, DNA complexed with cationic lipid, viral vectors and vector producer cell lines into normal and abnormal cells and tissues, generally by direct injection into a targeted site.

The aforementioned techniques for introducing polynucleotide, viral and other vectors into cells in culture, in animals and in patients can be used to develop, test and produce, as well as use vectors in accordance with the invention. For instance, cells containing a vector introduced by these methods can be used for producing the vector. In addition, cells containing a vector can be used as producer-cells and introduced into cells or tissues of an animal to produce the vector in situ.

Assay of DNA and Viral Replication

Replication of a polynucleotide, viral or other vector can be assayed by well-known techniques. Assays for replication of a vector in a cell generally involve detecting a polynucleotide, virions or infective virus. A variety of well-known methods that can be used for this purpose involve determining the amount of a labelled substrate incorporated into a polynucleotide during a given period in a cell.

When replication involves a DNA polynucleotide, $^3$H-thymidine often is used as the labelled substrate. In this case, the amount of replication is determined by separating DNA of the vector from the bulk of cellular DNA and measuring the amount of tritium incorporate specifically into vector DNA.

Replication of a polynucleotide vector also may be detected by lysing or permeating cells to release the polynucleotide, then isolating the polynucleotide and quantitating directly the DNA or RNA that is recovered. Polynucleotide replication also may be detected by quantitative PCR using primers that are specific for the assay polynucleotide.

Virions may be assayed by EM counting techniques well known to the art, by isolating the virions and determining protein and nucleic acid content, and by labelling viral genomic polynucleotides or virion proteins and determining the amount of virion from the amount of polynucleotide or protein.

It is well known that virions may not all be viable and where infectivity is important, infectious titer may be determined by cytopathic effect or plaque assay.

Any of these well-known techniques, among others, can be employed to assay replication of a vector in a cell or tissue in accordance with the invention. It will be appreciated that different techniques will be better suited to some vectors than others and to some cells or tissues than others.

Having thus described herein the invention in general terms, the following examples are presented to illustrate the invention. Examples 1–4 show the replacement of the constitutive E1A promoter on an adenoviral vector with a tumor-specific promoter. Constructs made this way have the E1a protein expressed only in tumor cells and therefore, will replicate only in tumor cells.

EXAMPLE 1

The Hepatoma-specific Promoter, α-Fetoprotein Promoter, Linked to E1a

The α-fetoprotein promoter has been previously shown to be highly active in hepatoma cells and silent in adult hepatocytes and other adult tissues. A 4.9 kb α-fetoprotein promoter containing construct was used to derive the promoter. Alternatively, the promoter could also be made based on available references.

Figure 1B:
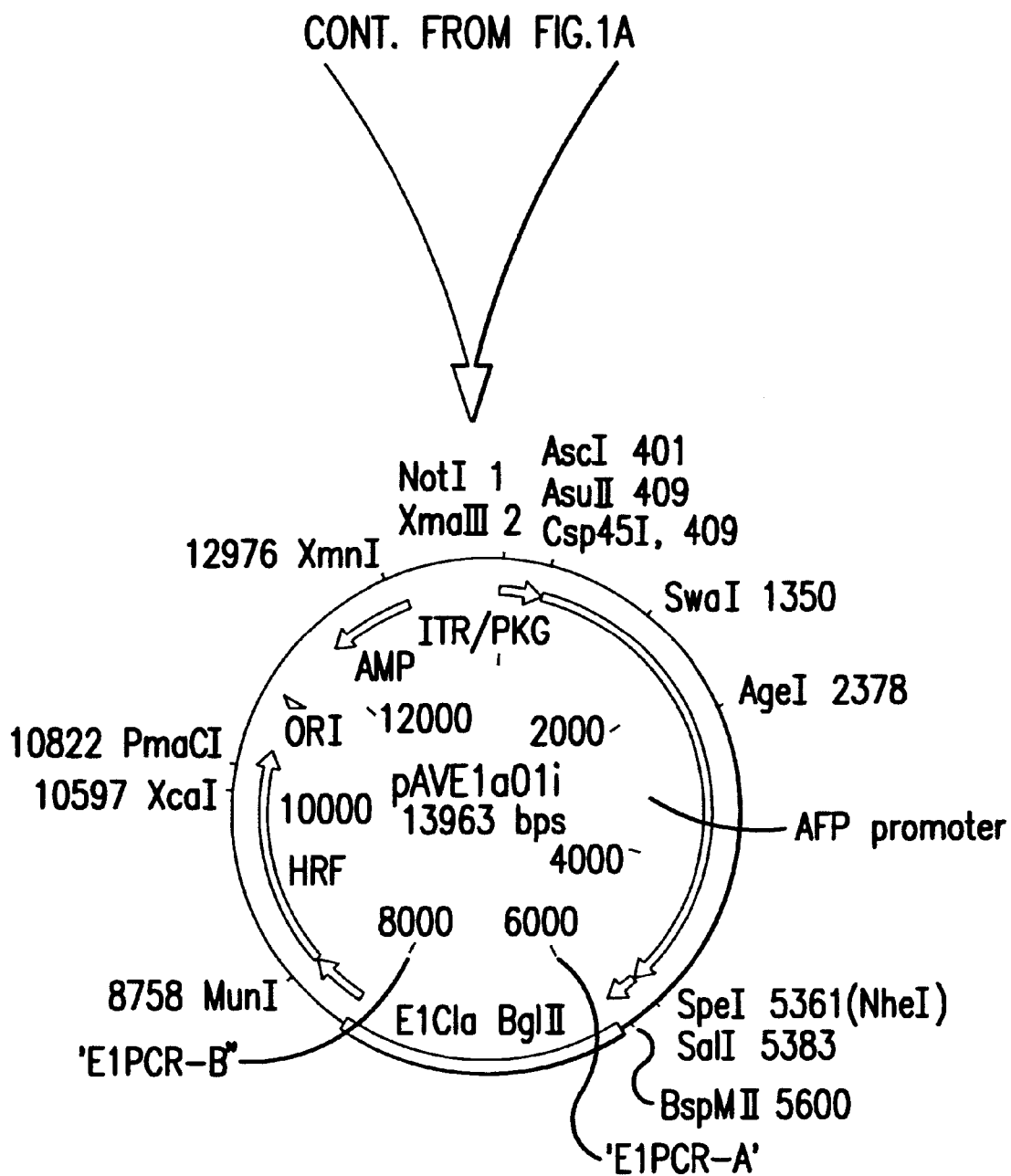

The adenovirus shuttle plasmid pAVSAFP.TK1 (a.k.a. pAVS21.TK1, FIG. 1), which has the TK gene under the control of the 4.9 kb α-fetoprotein promoter, was made exactly as described in FIGS. 11 and 12 of the U.S. patent application of Chiang et al. for "Gene Therapy of Hepatocellular Carcinoma Through Cancer-Specific Gene Expression", filed on May 18, 1995, which is incorporated herein by reference for its relevant teaching. pAVE1a02i which places the E1a/E1b genes under the control of the α-fetoprotein promoter in an adenovirus shuttle plasmid was cloned by purifying a restriction fragment which contained the E1a coding region only and all of E1b gene by cleaving the plasmid 380–280E1 (FIG. 1) with SpeI and MunI and ligating this to (pAVSAFP.TK1) cleaved with MunI and NheI. Plasmid SE280-E1, which contains the E1A ORF and all of E1b, was constructed as described in U.S. patent application Ser. No. 08/458,403 to Kadan et al. for "Improved Adenoviral Vectors and Producer Cells," filed Jun. 2, 1995, which is incorporated herein by reference for its relevant teaching. pAVE1a02i is cotransfected with the large ClaI fragment of Addl327 by standard methods into 293 cells to generate recombinant virus.

Construction of a Virus with the Hepatoma-specific AFP Promoter Operably Linked to the E1a Gene The adenovirus AVE1a04i was constructed by homologous recombination of the shuttle plasmid, pAVE1a04i (See FIG. 2), with the large (Cla1) fragment of AV1lacZ4 DNA in 293 cells. The construction of the plasmid pAVE1a02i is described above. The construction of pAVE1a04i is almost identical to that of pAVE1a02i. pAVE1a02i contains the entire AFP promoter. pAVE1a04i utilizes a derivative of this promoter, which has six silencer elements and a duplicated enhancer region.

The plasmid pAF(AB)$_2$(S$_d$)$_6$-CAT was constructed by placing six copies of the distal silencer immediately upstream of the basal 200 base pair AFP promoter. Two copies of the enhancer AB region, in opposite orientation, are placed immediately upstream of the silencer elements. This promoter, extending from the enhancer element through the basal AFP promoter, was used to make the AV/AFP short E1a virus with the shuttle plasmid described herein. The distal silencer element, the basal promoter, and the enhancer elements are as described in Nakabayashi et al. (*Molec. & Cell. Biol.* 11:5885–5893 (1991)).

The plasmid pAVE1a04i was grown in STBL2 cells and was purified by standard cesium banding methods prior to use in transfection. Genomic AV1lacZ4 DNA was isolated from cesium gradient-purified virus (herein described). The AV1lacZ4 purified virus was digested with proteinase K and the DNA isolated by phenol/chloroform extraction. The purified DNA was digested with Cla1 and the large fragment was isolated by gel electrophoresis and quantified. 5 µg of the plasmid pAVE1a04i and 2.5 µg of the large Cla1 fragment of AV1lacZ4 were co-transfected into 293 cells using a calcium phosphate-mediated transfection procedure (Promega, E1200 kit). The transfection plate was overlayered with a 1% agarose overlay and incubated until plaques formed. Once plaques had formed, they were picked and the virus was released into 500 µl of IMEM media by alternate cycles of freezing and thawing (5×). The eluted viral plaques were reamplified on A30 cells for 48 hours and then the cells were lysed for use in screening by PCR.

Figure 2A:
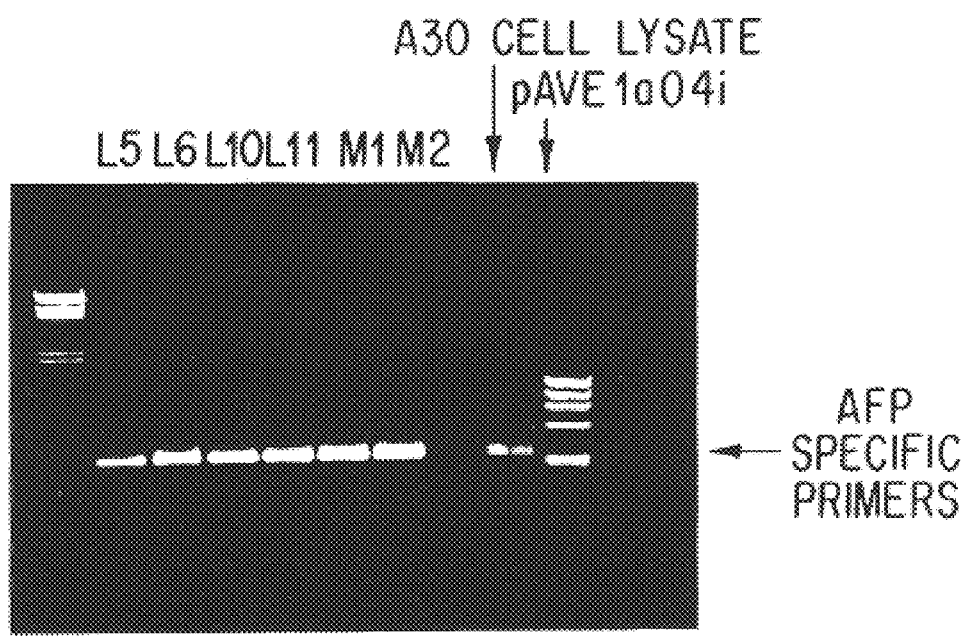
Figure 2B:
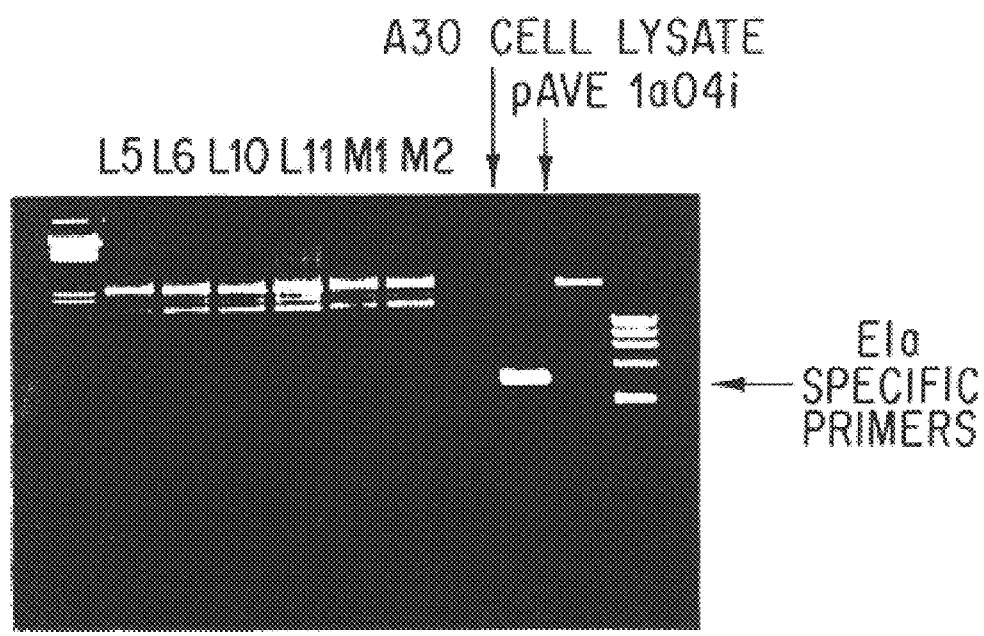
FIG. 2B shows that there was no contamination with wild-type virus.
Figure 2C:
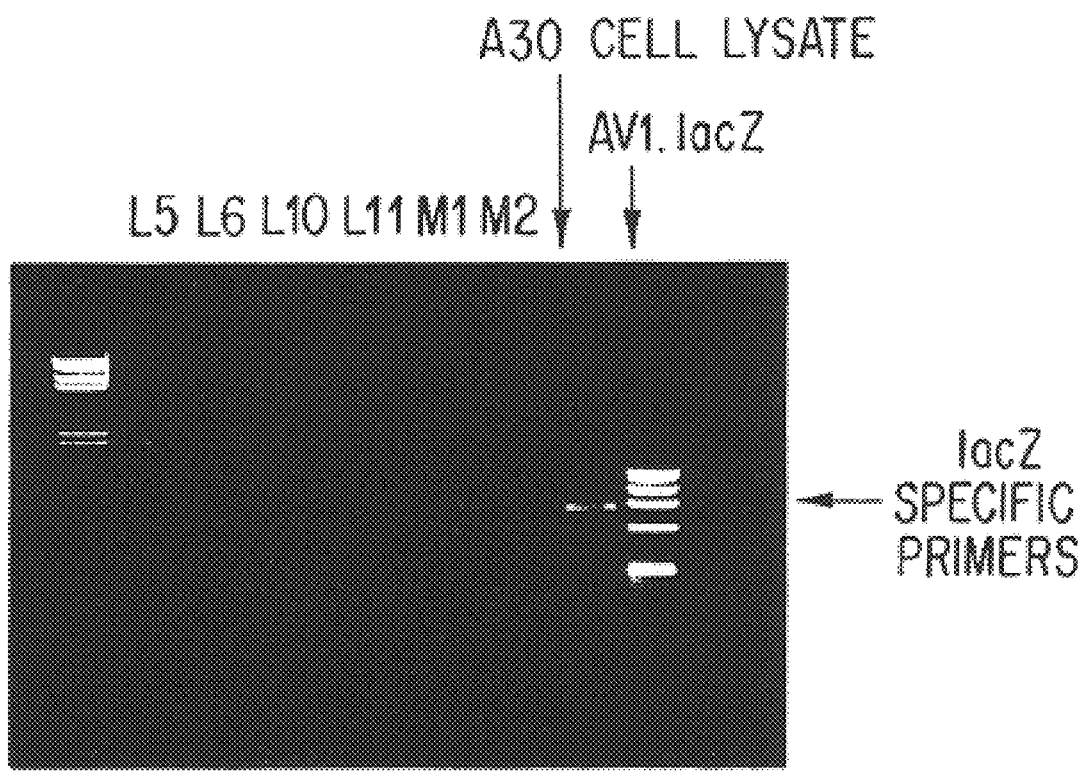
FIG. 2C shows that there was no contamination with AV1lacZ DNA.

Primers specific for the short AFP (sAFP) promoter in plasmid pAVE1a04i were used to identify the putative plaques. FIG. 2A shows that viral plaques contain a sAFP-specific band of the predicted molecular weight and specific for the sAFP primers. To confirm that this recombinant virus was not contaminated with Ad5dl327 (wild type), E1a primers were used. FIG. 2B demonstrates that no wild type virus was present and that pAVE1a04i plasmid sequences were present in the recombinant virus. FIG. 2C demonstrates that little or no AV1lacZ4 was present. The data indicate the construction of a virus with E1a under control of a tissue-specific promoter and that the virus is capable of replication in A30 cells.

Individual plaques were grown in A30 cells and analyzed by PCR for the presence of the AFP promoter (FIG. 2). The arrow indicates the AFP-specific band generated from PCR. The figure shows that the band is present in each of the viruses in the selected plaques (L6, L10, L11, M1 and M2). The control in the experiment was an A30 cell lysate, expected not to contain the band. The experiment also included the PCR reaction with the plasmid pAVE1a04i (the shuttle plasmid from which the virus was made and which therefore should produce the AFP-specific fragment). Thus, FIG. 2A confirms the presence of a recombinant virus containing the AFP promoter. FIGS. 2B and 2C confirm that these results were not the result of contamination in the individual plaques. FIG. 2B uses E1a-specific primers to detect the presence of any contaminating wild-type virus. The arrow shows the band produced with E1a-specific primers. The figure shows that none of the recombinant viruses produced the relevant band. FIG. 2C confirms that there is no AV1.lacZ contamination in the viral plaques (since the viruses were made using AV1.lacZ DNA). The figure indicates that only the lane containing AV1.lacZ DNA produced the band.

Tissue-specific Viral Replication

Cytopathic viral lysate of this virus ("AVAFPE1a") was serially diluted in logs of 10 on A549.30 cells, A549 cells, and HuH 7 cells. A549.30 cells express the E1a from the glucocorticoid receptor element (GRE) promoter in the presence of dexamethasone since this construct is integrated into the genome of this cell line. Thus, any E1a-deleted virus or any virus not expressing E1a should be able to replicate in this cell line. This has previously been shown for E1-deleted vectors (unpublished communication). As can be seen from FIGS. 3A and 3D, the AVAFPE1a vector replicates in the infected cells as indicated by characteristic cytopathic effects and spreading of cell death. The A549 cells do not express AFP and should not be capable of transactivating the AFP promoter. In addition, A549 cells do not express E1a. Thus, AVAFPE1a should not be able to replicate in this cell line. As can be seen from FIGS. 3B and 3E, both uninfected and infected wells appear identical with no characteristic cytopathic effects or spreading observed at all dilutions tested. HuH 7 cells do express AFP, should transactivate the AFP promoter, and should make E1a with subsequent replication. As shown in FIGS. 3C and 3F, AVAFPE1a clearly replicates, as indicated by the cytopathic effects. In addition, on several wells of infected HuH 7 cells, the replication began with a single plaque which spread throughout the rest of the well within one week. All HuH 7 wells showing cytopathic effects were tested by PCR and demonstrated to be free of wild-type virus and AV1lacZ4 virus, and to contain an intact AFP promoter. These data clearly indicate that a virus has been constructed that is capable of replicating specifically in tumor cells expressing AFP.

EXAMPLE 2

The Breast Cancer-specific DF3-Mucin Enhancer

The DF3 breast carcinoma associated antigen (MUC1) is highly overexpressed in human breast carcinomas. The expression of the gene is regulated at the transcriptional level. The DNA sequence between −485–588 is necessary and sufficient for conferring a greater than 10-fold increase in transcription of the reporter gene CAT when placed immediately upstream of a basal promoter derived from the Herpesvirus TK promoter in transient transfection assays performed in the human breast cancer cell line MCF-7. A specific transcription factor which binds to this region of DNA has also been found within cells derived from the breast cancer cell line MCF-7 but not a non-breast cancer cell line HL-60. The same region of DNA has been found to promote breast cancer-specific expression of the TK gene in the context of a retroviral construct or an adenoviral construct.

The DF3 enhancer from −598 to −485 (obtained from GenBank) was synthesized by constructing four oligonucleotides synthesized in such a way as they would overlap and anneal. The oligonucleotides are shown in Table 1. Additional restriction sites were added on both ends for future ease of cloning. One end was kept blunt to enable cloning into the SmaI site of the vector pTK-Luc. This vector contains the basal promoter of the Herpesvirus TK gene which gives low level basal activity in a variety of cells. It was used as a source of this basal promoter. The other end had an overlapping BglII site for ease in cloning into the BglII site of pTK-Luc. 1,000 ng of each oligonucleotide were annealed in 0.017 M Tris, pH 8.0, 0.16 M NaCl in a total volume of 26.5 μl by heating at 95° C. for two minutes and allowing to cool to room temperature after several hours. Finally, 1 μl of this mixture was ligated to 100 ng of previously SmaI/BglII-and glass milk (BIO 101)-purified vector by standard conditions. Following transformation into DH5α cells (GIBCO), colonies were screened for the presence of the insert by standard restriction digests. DNA derived from this vector is then cleaved with HindIII and blunted by Klenow. It is then cleaved by AscI. This fragment, which contains the DF3 enhancer lined to the basal TK promoter, is then purified by agarose gel electrophoresis and glass milk and ligated to the plasmid pAVE1a02i, cleaved with Spe I and blunt-ended with AscI and purified as above. The resultant plasmid has the E1A gene product under the control of the DF3 enhancer and basal TK promoter and is in an adenoviral shuttle plasmid. 5 μg of this plasmid, pAVE1a03i, is cotransfected with 5 μg of the right ClaI fragment arm, derived from Addl327, into 293 cells. Plaques are screened for the expected recombinant virus by standard methods.

A crude virus lysate is used to infect MCF-7 at an MOI of 10. Virus stocks are confirmed to replicate specifically in breast cancer cells by standard methods. Virus is scaled up in MCF-7 cells and/or 293 cells as described for scaleup and purification on 293 cells. Virus stocks are tested for replication in vivo by using a mode mouse model of MCF-7 and, as a negative control, a cervical cancer (Hela) derived tumor is used. Virus is tested for a recombinational event in 293 cells which would generate a wild-type virus by PCR assay of the original E1A promoter which would only be in a wild-type virus. A variety of other human and rat breast cancer cell lines and non-related cell lines are also tested. The TK gene can be inserted into the E3 region and have TK driven either by the E1A-dependent promoter present there or under the control of the RSV or CMV promoter.

EXAMPLE 3

The Melanoma-specific Tyrosinase Promoter

PCR primers and PCR were used to clone a fragment of DNA 800 bp upstream of the tyrosinase gene from mouse genomic DNA using PFU and the described primers as described by Stratogene. The resultant PCR fragment was cloned into pCRSCRIPT and then recloned into pAVE1a02i by digesting the new plasmid with AscI/SpeI and pAVE1a01i with AscI/SpeI and ligating the two together. The final shuttle plasmid, pAVE1a04i, which has E1a/E1b under the control of the tyrosinase promoter, is utilized to make a recombinant virus identically as described above.

EXAMPLE 4

The Colon Cancer-specific CEA Promoter

The CEA promoter was cloned from human genomic DNA as described above and cloned in a similar way into the pAVE1a01i plasmid using the primers shown in Table 1. The final shuttle plasmid, pAVE1a05i, is used to generate recombinant virus as described above.

EXAMPLE 5

A. Replacing the Promoter of E2a on an Adenoviral Vector with a Tumor Specific Promoter Constructs made as above will have the E2a protein (essential for viral replication expressed only in tumor cells.

Therefore, replication of the vector occurs only in tumor cells. All four of these very specific promoters (in the examples above) are used to place the E2a coding region obtained from pSE280-E2a (see U.S. patent application to Ser. No. 08/458,403 of Kaden et al., "Improved adenoviral vectors and producer cells" filed Jun. 2, 1995) under the control of that tumor-specific promoter. The resultant plasmid is recombined with Addl327, using standard methods of homologous recombination. The final virus is grown in the cell lines described in the aforementioned patent application or in the tumor specific cell lines. The E2a protein, because it is needed in stoichiometric amounts, has the ability to regulate the degree of replication over a broad range. This is desirable for therapy. The methods used are the same as those described for E1a. The difference is that a shuttle plasmid is used that places E2a under the control of the tumor specific promoter and returns it to a virus backbone (by homologous recombination) that has the E2a and E3 genes deleted.

B. Replacement of other Therapeutic Toxic Genes into the Tumor-specific Replication Competent Vectors Genes such as TK, cytokines, or any therapeutic genes can be placed into the E3 region of the vector backbone by standard plasmid construction and homologous recombination. Those genes can be placed under the control of an E1a-dependent promoter, or a constitutive promoter such as RSV or CMV.

The disclosures of all patents, publications (including published patent applications), and database accession numbers referred to in this specification are specifically incorporated herein by reference in their entirety to the same extent as if each such individual patent, publication, and database accession numbers were specifically and individually indicated to be incorporated by reference in its entirety.

TABLE 1

Oligonucleotide Primers for Constructing Tissue-Specific Promoters

```
1. DF3 (Breast Cancer)
5' GGG CGC GCC CTG GAA AGT CCG GCT GGG GCG
   GGG ACT GTG GGT TTC AGG GTA GAA CTG CGT
   GTG GAA          3'(SEQ ID NO:1)
5' CGG GAC AGG GAG CGG TTA GAA GGG TGG GGC
   TAT TCC GGG AAG TGG TGG GGG GAG GGA ACT
   AGT A            3'(SEQ ID NO:2)
5' GAT CTA CTA GTT CCC TCC CCC CAC CAC TTC
   CCG GAA TAG CCC CAC CCT TCT AAC CGC TCC
   CTG              3'(SEQ ID NO:3)
5' TCC CGT TCC ACA CGC AGT TCT ACC CTG AAA
   CCC ACA GTC CCC GCC CCA GCC GGA CTT TCC
   AGG GCG CGC CC   3'(SEQ ID NO:4)
2. Tyrosinase (Melanoma)
5' GAC CCG GGC GCG CCG GAG CAG TGC TAT TCA
   AAC CAT CCA G    3'(SEQ ID NO:5)
5' CGA GAT CTA CTA GTT CTG CAC CAA TAG GTT
   AAT GAG TGT C    3'(SEQ ID NO:6)
3. CEA Promoter (Hepatocellular Carcinoma)
5' GAC CCG GGC GCG CCT CTG TCA CCT TCC TGT
   TGG              3'(SEQ ID NO:7)
5' CGA GAT CTA CTA GTT CTC TGC TGT CTG CTC
   TGT C            3'(SEQ ID NO:8)
```

What is claimed is:

1. A tissue-specific replication-conditional adenovirus vector comprising a heterologous tissue-specific transcriptional regulatory sequence operably linked to the coding region of a gene that is essential for replication of said vector.

2. The vector of claim 1, wherein the transcriptional regulatory sequence is selected from the group consisting of promoters and enhancers.

3. The vector of claim 2, wherein said transcriptional regulatory sequence is a promoter selected from the group consisting of an α-fetoprotein promoter, a DF3 promoter, a tyrosinase promoter, a CEA promoter, a surfactant promoter, and an ErbB2 promoter.

4. The vector of claim 1, wherein said coding region is selected from the group consisting of E1a, E1b, E2a, E2b and E4 coding regions.

5. The vector of claim 1, wherein said vector contains a heterologous coding sequence that is capable of being expressed from said vector.

6. The vector of claim 4, wherein said coding region is the E1a coding region.

7. The vector of claim 4, wherein said coding region is the E1b coding region.

8. The vector of claim 4, wherein said coding region is the E2a coding region.

9. The vector of claim 4, wherein said coding region is the E2b coding region.

10. The vector of claim 4, wherein said coding region is the E4 coding region.

11. The vector of claim 6, wherein said transcriptional regulatory sequence is a tumor-specific promoter.

12. The vector of claim 7, wherein said transcriptional regulatory sequence is a tumor-specific promoter.

13. The vector of claim 8, wherein said transcriptional regulatory sequence is a tumor-specific promoter.

14. The vector of claim 9, wherein said transcriptional regulatory sequence is a tumor-specific promoter.

15. The vector of claim 10, wherein said transcriptional regulatory sequence is a tumor-specific promoter.

16. A replication-conditional adenovirus vector comprising the coding region of an adenovirus early gene essential for propagation under the transcriptional control of a carcinoembryonic antigen (CEA) response element.

17. A method for propagating an adenovirus specific for reproductive tract tumor cells, said method comprising directly administering the adenovirus of claim 16 to CEA-expressing reproductive tract tumor cells, whereby said adenovirus is propagate.

18. The vector of claim 16, wherein the coding region of said early gene is selected from the group consisting of E1a, E1b, E2a, E2b and E4 coding regions.

19. The vector of claim 1, wherein said transcriptional regulatory sequence is a tumor-specific regulatory sequence.

20. The vector of claim 19, wherein said tumor-specific regulatory sequence is a tumor-specific promoter.

21. The vector of claim 18, wherein said coding region is the E1a coding region.

22. The vector of claim 18, wherein said coding region is the E1b coding region.

23. The vector of claim 18, wherein said coding region is the E2a coding region.

24. The vector of claim 18, wherein said coding region is the E2b coding region.

25. The vector of claim 18, wherein said coding region is the E4 coding region.

26. The vector of claim 21, wherein said transcriptional regulatory sequence is a tumor-specific promoter.

27. The vector of claim 22, wherein said transcriptional regulatory sequence is a tumor-specific promoter.

28. The vector of claim 23, wherein said transcriptional regulatory sequence is a tumor-specific promoter.

29. The vector of claim 24, wherein said transcriptional regulatory sequence is a tumor-specific promoter.

30. The vector of claim 25, wherein said transcriptional regulatory sequence is a tumor-specific promoter.

31. An isolated cell containing a tissue-specific replication-conditional adenovirus vector, said vector comprising a heterologous tissue-specific transcriptional regulatory sequence operably linked to the coding region of a gene that is essential for replication of said vector, wherein said transcriptional regulatory sequence functions in said cell so that replication of the vector occurs in said cell.

32. The isolated cell of claim 31, wherein said transcriptional regulatory sequence is selected from the group consisting of promoters and enhancers.

33. The isolated cell of claim 32, wherein said transcriptional regulatory sequence is a promoter selected from the group consisting of an α-fetoprotein promoter, a DF3 promoter, a tyrosinase promoter, a CEA promoter, a surfactant promoter, and an ErbB2 promoter.

34. The isolated cell of claim 31, wherein said cell is a tumor cell.

35. The isolated cell of claim 31, wherein said coding region that is operably linked to said transcriptional regulatory sequence is selected from the group consisting of E1a, E1b, E2a, E2b and E4 coding regions.

36. The isolated cell of claim 31, wherein said vector further comprises a heterologous gene.

37. The isolated cell of claim 36, wherein the product of said heterologous gene provides anti-tumor activity in the cells of a target tissue.

38. The isolated cell of claim 35, wherein said coding region is the E1a coding region.

39. The isolated cell of claim 35, wherein said coding region is the E1b coding region.

40. The isolated cell of claim 35, wherein said coding region is the E2a coding region.

41. The isolated cell of claim 35, wherein said coding region is the E2b coding region.

42. The isolated cell of claim 35, wherein said coding region is the E4 coding region.

43. The isolated cell of claim 38, wherein said transcriptional regulatory sequence is a tumor-specific promoter.

44. The isolated cell of claim 39, wherein said transcriptional regulatory sequence is a tumor-specific promoter.

45. The isolated cell of claim 40, wherein said transcriptional regulatory sequence is a tumor-specific promoter.

46. The isolated cell of claim 41, wherein said transcriptional regulatory sequence is a tumor-specific promoter.

47. The isolated cell of claim 42, wherein said transcriptional regulatory sequence is a tumor-specific promoter.

48. A method of producing a tissue-specific replication-conditional adenovirus vector, said vector comprising a heterologous tissue-specific transcriptional regulatory sequence operably linked to the coding region of a gene that is essential for replication of said vector, comprising culturing the isolated cell of claim 31 and recovering said vector from said cell.

49. An isolated cell containing a tissue-specific replication-conditional adenovirus virion, said virion comprising a heterologous tissue-specific transcriptional regulatory sequence operably linked to the coding region of a gene that is essential for replication of said virion, wherein said transcriptional regulatory sequence functions in said cell so that replication of the virion occurs in said cell.

50. The isolated cell of claim 49, wherein said transcriptional regulatory sequence is selected from the group consisting of promoters and enhancers.

51. The isolated cell of claim 50, wherein said transcriptional regulatory sequence is a promoter selected from the group consisting of an α-fetoprotein promoter, a DF3 promoter, a tyrosinase promoter, a CEA promoter, a surfactant promoter, and an ErbB2 promoter.

52. The isolated cell of claim 49, wherein said cell is a tumor cell.

53. The isolated cell of claim 49, wherein said coding region that is operably linked to said transcriptional regulatory sequence is selected from the group consisting of E1a, E1b, E2a, E2b and E4 coding regions.

54. The isolated cell of claim 49, wherein said virion further comprises a heterologous gene.

55. The isolated cell of claim 54, wherein the product of said heterologous gene provides anti-tumor activity in the cells of a target tissue.

56. A method of producing a tissue-specific replication-conditional adenovirus virion, said virion comprising a heterologous tissue-specific transcriptional regulatory sequence operably linked to the coding region of a gene that is essential for replication of said virion, comprising culturing the isolated cell of claim 49 and recovering said virion from said cell.

57. The isolated cell of claim 31, wherein said transcriptional regulatory sequence is a tumor-specific regulatory sequence.

58. The isolated cell of claim 57, wherein said tumor-specific regulatory sequence is a tumor-specific promoter.

59. The isolated cell of claim 49, wherein said transcriptional regulatory sequence is a tumor-specific promoter.

60. The isolated cell of claim 59, wherein said transcriptional regulatory sequence is a tumor-specific regulatory sequence.

61. The isolated cell of claim 53, wherein said coding region is the E1a coding region.

62. The isolated cell of claim 53, wherein said coding region is the E1b coding region.

63. The isolated cell of claim 53, wherein said coding region is the E2a coding region.

64. The isolated cell of claim 53, wherein said coding region is the E2b coding region.

65. The isolated cell of claim 53, wherein said coding region is the E4 coding region.

66. The isolated cell of claim 61, wherein said transcriptional regulatory sequence is a tumor-specific promoter.

67. The isolated cell of claim 62, wherein said transcriptional regulatory sequence is a tumor-specific promoter.

68. The isolated cell of claim 63, wherein said transcriptional regulatory sequence is a tumor-specific promoter.

69. The isolated cell of claim 64, wherein said transcriptional regulatory sequence is a tumor-specific promoter.

70. The isolated cell of claim 65, wherein said transcriptional regulatory sequence is a tumor-specific promoter.

71. A tissue-specific replication-conditional adenoviral virion comprising a heterologous tissue-specific transcriptional regulatory sequence operably linked to the coding region of a gene that is essential for replication of said virion.

72. The virion of claim 71, wherein the transcriptional regulatory sequence is selected from the group consisting of promoters and enhancers.

73. The virion of claim 72, wherein said transcriptional regulatory sequence is a promoter selected from the group consisting of an α-fetoprotein promoter, a DF3 promoter, a tyrosinase promoter, a CEA promoter, a surfactant promoter, and an ErbB2 promoter.

74. The virion of claim 71, wherein said transcriptional regulatory sequence is a tumor-specific regulatory sequence.

75. The virion of claim 74, wherein said tumor-specific regulatory sequence is specific promoter.

76. The virion of claim 71, wherein said coding region is selected from the group consisting of E1a, E1b, E2a, E2b and E4 coding regions.

77. The virion of claim 71, wherein said virion contains a heterologous coding sequence that is capable of being expressed from said virion.

78. The virion of claim 76, wherein said coding region is the E1a coding region.

79. The virion of claim 76, wherein said coding region is the E1b coding region.

80. The virion of claim 76, wherein said coding region is the E2a coding region.

81. The virion of claim 76, wherein said coding region is the E2b coding region.

82. The virion of claim 76, wherein said coding region is the E4 coding region.

83. The virion of claim 78, wherein said transcriptional regulatory sequence is a tumor-specific promoter.

84. The virion of claim 79, wherein said transcriptional regulatory sequence is a tumor-specific promoter.

85. The virion of claim 80, wherein said transcriptional regulatory sequence is a tumor-specific promoter.

86. The virion of claim 81, wherein said transcriptional regulatory sequence is a tumor-specific promoter.

87. The virion of claim 82, wherein said transcriptional regulatory sequence is a tumor-specific promoter.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 66 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 1:

GGGCGCGCCC TGGAAAGTCC GGCTGGGGCG GGGACTGTGG GTTTCAGGGT AGAACTGCGT    60

GTGGAA    66

(2) INFORMATION FOR SEQ ID NO: 2:

(i) SEQUENCE CHARACTERISTICS:
      (A) LENGTH: 64 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 2:

CGGGACAGGG AGCGGTTAGA AGGGTGGGGC TATTCCGGGA AGTGGTGGGG GGAGGGAACT    60

AGTA    64

(2) INFORMATION FOR SEQ ID NO: 3:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

```
GATCTACTAG TTCCCTCCCC CCACCACTTC CCGGAATAGC CCCACCCTTC TAACCGCTCC        60

CTG                                                                     63
```

(2) INFORMATION FOR SEQ ID NO: 4:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

```
TCCCGTTCCA CACGCAGTTC TACCCTGAAA CCCACAGTCC CCGCCCCAGC CGGACTTTCC        60

AGGGCGCGCC C                                                            71
```

(2) INFORMATION FOR SEQ ID NO: 5:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

```
GACCCGGGCG CGCCGGAGCA GTGCTATTCA AACCATCCAG                              40
```

(2) INFORMATION FOR SEQ ID NO: 6:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

```
CGAGATCTAC TAGTTCTGCA CCAATAGGTT AATGAGTGTC                              40
```

(2) INFORMATION FOR SEQ ID NO: 7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

```
GACCCGGGCG CGCCTCTGTC ACCTTCCTGT TGG                                     33
```

```
(2) INFORMATION FOR SEQ ID NO: 8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

CGAGATCTAC TAGTTCTCTG CTGTCTGCTC TGTC                                              34
```